(12) United States Patent
Petersen et al.

(10) Patent No.: US 11,279,771 B2
(45) Date of Patent: *Mar. 22, 2022

(54) ANTIBODIES CAPABLE OF BINDING TWO EPITOPES ON TISSUE FACTOR PATHWAY INHIBITOR (1-161)

(71) Applicant: Novo Nordisk A/S, Bagsvaerd (DK)

(72) Inventors: Helle Heibroch Petersen, Koebenhavn V (DK); Berit Olsen Krogh, Roedovre (DK); Jens Breinholt, Dyssegaerd (DK); Mikael Kofod-Hansen, Broenshoej (DK); Ida Hilden, Vanloese (DK)

(73) Assignee: NOVO NORDISK A/S, Bagsvaerd (DK)

( * ) Notice: Subject to any disclaimer, the term of this patent is extended or adjusted under 35 U.S.C. 154(b) by 115 days.

This patent is subject to a terminal disclaimer.

(21) Appl. No.: 15/508,229

(22) PCT Filed: Sep. 17, 2015

(86) PCT No.: PCT/EP2015/071359
§ 371 (c)(1),
(2) Date: Mar. 2, 2017

(87) PCT Pub. No.: WO2016/042093
PCT Pub. Date: Mar. 24, 2016

(65) Prior Publication Data
US 2017/0260289 A1 Sep. 14, 2017

(30) Foreign Application Priority Data

Sep. 17, 2014 (EP) .................................... 14185138

(51) Int. Cl.
*C07K 16/38* (2006.01)
*A61K 39/00* (2006.01)

(52) U.S. Cl.
CPC ........ *C07K 16/38* (2013.01); *A61K 2039/507* (2013.01); *C07K 2317/24* (2013.01); *C07K 2317/31* (2013.01); *C07K 2317/34* (2013.01); *C07K 2317/53* (2013.01); *C07K 2317/55* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,193,982 | A  | * | 3/1980  | Avrameas | G01N 33/531 530/391.1 |
|---|---|---|---|---|---|
| 8,361,469 | B2 | * | 1/2013  | Hilden | A61P 7/00 424/145.1 |
| 10,457,743 | B2 | * | 10/2019 | Thorn Clausen | A61P 7/04 |
| 2002/0197667 | A1 |   | 12/2002 | Innis et al. |  |
| 2011/0268745 | A1 | * | 11/2011 | Hilden | C07K 16/18 424/158.1 |
| 2011/0318356 | A1 |   | 12/2011 | Hilden et al. |  |
| 2012/0190834 | A1 |   | 7/2012  | Schaub et al. |  |
| 2012/0269817 | A1 |   | 10/2012 | Wang et al. |  |
| 2013/0142804 | A1 |   | 6/2013  | Hilden et al. |  |
| 2013/0252896 | A1 |   | 9/2013  | Dockal et al. |  |
| 2013/0267584 | A1 |   | 10/2013 | Dockal et al. |  |

FOREIGN PATENT DOCUMENTS

| AU | 2014200227 A1 | 1/2014 | |
| WO | 2010017196 A2 | 2/2010 | |
| WO | 2010072691 A1 | 7/2010 | |
| WO | 2012001087 A1 | 1/2012 | |
| WO | 2012135671 A2 | 10/2012 | |
| WO | WO-2012135671 A2 * | 10/2012 | ............. C07K 16/38 |
| WO | 13148248 A1 | 10/2013 | |

OTHER PUBLICATIONS

Edwards et al., J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Agerso H. et al., Pharmacokinetics of an anti-TFPI monoclonal antibody (concizumab) blocking the TFPI interaction with the active site of FXa in Cynomolgus monkeys after iv and sc administration, European Journal of Pharmaceutical Sciences, 2014, vol. 56, pp. 65-69.
Baugh R. J. et al., Regulation of Extrinsic Pathway Factor Xa Formation by Tissue Factor Pathway Inhibitor, The Journal of Biological Chemistry, 1998, vol. 273, No. 8, 4378-4386, SPEC.
Glaven R. H. et al., Linking Single Domain Antibodies that Recognize Different Epitopes on the Same Target, Biosensors, 2012, vol. 2, No. 4, 43-56, EP A SR, WO SR.
Hilden I st al., Hemostatic effect of a monoclonal antibody mAb 2021 blocking the interaction between FXa and TFPI in a rabbit hemophilia model, Blood, 2012, vol. 119, No. 24, 5871-5878, EP A SR, WO SR.

(Continued)

*Primary Examiner* — Michael Szperka
(74) *Attorney, Agent, or Firm* — Rosemarie R. Wilk-Orescan

(57) ABSTRACT

The application discloses bispecific TFPI antibodies that are capable of specifically and simultaneously binding two epitopes within TFPI (1-161). Such bispecific antibodies strongly enhance thrombin generation by neutralising TFPI, even where the concentration of TFPI is elevated. Bispecific antibodies of the invention or compositions comprising them may be used for the treatment of subjects with a coagulopathy.

6 Claims, 3 Drawing Sheets

Specification includes a Sequence Listing.

(56) References Cited

OTHER PUBLICATIONS

Kelton C et al., Anti-EGFR biparatopic-SEED antibody has enhanced combination-activity; in a single molecule, Archives of Biochemistry and Biophysics, 2012, vol. 526, No. 2, 219-225, EP A SR, WO SR.

Petersen L. C. et al., Hemostatic properties of a TFPI antibody, Thrombosis Research, 2012, vol. 129, No. Suppl. 2, S44-S45, EP A SR, WO SR.

Petersen L. C. et al., Inhibitory properties of separate recombinant Kunitz-type-protease-inhibitor domains from tissue-factor-pathway inhibitor, European Journal of Biochemistry, 1996, vol. 235, No. 1-2, 310-316, EP A SR, WO SR.

Asuka Sakata et al., "Tissue factor pathway inhibitor (TFPI): The basis of Tissue factor pathway inhibitor ITFPI)," Journal of Thrombosis and H, 2014, vol. 25, No. 1, pp. 5-10.

* cited by examiner

ANTIBODIES CAPABLE OF BINDING TWO EPITOPES ON TISSUE FACTOR PATHWAY INHIBITOR (1-161)

CROSS-REFERENCE TO RELATED APPLICATIONS

This application is a 35 U.S.C. § 371 National Stage application of International Application No. PCT/EP2015/071359 (WO 2016/042093), filed Sep. 17, 2015, which claimed priority of European Patent Application No. 14185138.6, filed Sep. 17, 2014; the contents of all above-named applications are incorporated herein by reference.

FIELD OF THE INVENTION

The present invention relates to bispecific antibodies, and compositions thereof, that are capable of simultaneously binding two epitopes within the N-terminal region (residues 1-161) of tissue factor pathway inhibitor (TFPI). The invention also relates to the pharmaceutical and therapeutic uses of such antibodies.

The instant application contains a Sequence Listing which has been submitted in ASCII format via EFS-Web and is hereby incorporated by reference in its entirety. Said ASCII copy, created on Mar. 1, 2017, is named 140072US01_SeqList.txt and is 48 kilobytes in size. No new matter is added.

BACKGROUND

In a bleeding individual, coagulation is initiated by the Tissue Factor/Factor Vila (TF/FVIIa) complex when extravascular TF is exposed to FVIIa in the blood. TF/FVIIa complex formation leads to the activation of Factor X (FX) to FXa which, together with activated Factor V (FVa), generates a limited amount of thrombin. Small amounts of thrombin activate platelets which, in turn, results in the surface exposure of platelet phospholipids that support the assembly and binding of the tenase complex composed of activated Factor VIII (FVIIIa) and Factor IX (IXa). The tenase complex is a very efficient catalyst of FX activation and FXa generated in this second step serves as the active protease in the FVa/FXa pro-thrombinase complex responsible for the final thrombin burst. Thrombin cleaves fibrinogen to generate fibrin monomers, which polymerise to form a fibrin network which seals the leaking vessel and stops the bleeding. The rapid and extensive thrombin burst is a prerequisite for the formation of a solid and stable fibrin clot.

An inadequate propagation of FXa and thrombin generation caused by FVIII or FIX deficiency is the reason underlying the bleeding diathesis in haemophilia A and B patients, respectively. In people with haemophilia, FXa generation is primarily driven by the TF/FVIIa complex because FVIII or FIX deficiency only leads to rudimentary FXa generation by the tenase complex. TF/FVIIa-mediated activation of FX to FXa is, however, temporary because tissue factor pathway inhibitor (TFPI) inhibits Factor Xa and the TF/FVIIa complex in an auto-regulatory loop. Feed-back inhibition leads to formation of a TF/FVIIa/FXa/TFPI complex.

Neutralizing TFPI inhibition prolongs TF/FVIIa-mediated activation of FX during initiation of coagulation, and thereby it promotes haemostasis in people with haemophilia with an inadequate FXa generation caused by impaired tenase activity due to e.g. FVIII or FIX deficiency.

Following initiation of coagulation, TF/FVIIa-mediated FXa generation is tightly down-regulated by TFPI. TFPI is a slow tight-binding competitive inhibitor which regulates FX activation and activity through inhibition of both TF-FVIIa and FXa. TF/FVIIa is inhibited by TFPI in a process which as a rate limiting step involves TFPI inhibition of FXa, either when FXa is bound to the TF/FVIIa complex or bound in its near vicinity on the membrane (Baugh et al., 1998, *JBC*, 273: 4378-4386). TFPI inhibition of FXa occurs in a biphasic reaction that initially leads to a loose TFPI-FXa complex which slowly rearranges to a tight binding TFPI-FXa complex where the second Kunitz-type inhibitor domain of TFPI (KPI-2) binds and blocks the active site of FXa. The first Kunitz-type inhibitor domain of TFPI (KPI-1) contributes to the formation of the tight TFPI-FXa complex and it directly binds and blocks the active site of TF-bound FVIIa.

Antibodies that are capable of binding TFPI are known in the art. For example, WO2010/072691, WO2012/001087 and WO2012/135671 disclose monoclonal antibodies (mAbs), each of which is capable of binding to one specific epitope of TFPI. The following limitations may apply to such an antibody that targets a single TFPI epitope—e.g. on a KPI domain—which is typically restricted to the paratope area of an antibody defined by a single variable region. First of all, the final inhibition of the TF/FVIIa/FXa complex is dependent on several interactions between complementary areas scattered over TFPI and the TF/FVIIa/FXa complex. This applies not only to the direct binding of KPI-1 and KPI-2 of TFPI to the active sites of FVIIa and FXa, respectively, but also to interactions with TF/FVIIa/FXa exosites which involve regions of the N- and C-terminal regions of TFPI. A monoclonal antibody that binds, for example, a single KPI may not be capable of completely blocking all inhibitory functions of TFPI, particularly at physiologically elevated concentrations of TFPI. Secondly, the efficacy of a monospecific antibody may be hampered by the affinity of the antibody and/or the flexibility of the TPFI molecule, both of which would require dosing of the former to be high. Thirdly, targeting TFPI with a monoclonal antibody may cause TFPI to accumulate in the circulation as a result of a reduced renal clearance of the TFPI-mAb complex, or as a result of other clearance mechanisms which are reduced due to TFPI-mAb complex formation.

The inventors envisage that the bispecific antibodies that are disclosed herein may address such limitations.

SUMMARY

The current invention relates to a bispecific antibody capable of specifically binding a first epitope and a second epitope within positions 1 to 161 of human TFPI (SEQ ID NO: 1).

In one aspect the first epitope of the bispecific antibody may be within positions 1-96, such as within positions 1-76, such as within the Kunitz-type 1 inhibitor (KPI-1) domain (residues 26-76) of human TFPI. The KPI-1 epitope may comprise one or more of amino acid residues Arg 41, Arg 65 and/or Glu 67 of SEQ ID NO: 1, and may further comprise one or more of amino acid residues Leu 16, Pro 17, Leu 19, Lys 20, Leu 21, Met 22, Phe 25, Cys 35, Ala 37, Met 39, Tyr 56, Gly 57, Gly 58, Cys 59, Glu 60, Gly 61, Asn 62, Gin 63, Phe 66, Glu 71 and Met 75 of SEQ ID NO: 1.

In one aspect the second epitope of the bispecific antibody may be within positions 77-161, such as within positions 97-161, such as within the Kunitz-type inhibitor 2 (KPI-2) domain (residues 97-147) of human TFPI. The KPI-2 epitope may comprise amino acid residue Arg 107 of SEQ ID NO: 1 and may further comprise one or more of amino acid residues Glu 100, Glu 101, Asp 102, Pro 103, Tyr 109, Thr 111, Tyr 113, Phe 114, Asn 116, Gln 118, Gln 121, Cys 122, Glu 123, Arg 124, Phe 125, Lys 126 and Leu 140 of SEQ ID NO: 1.

The bispecific antibody of the current invention may be in IgG format such as full length IgG format, or it may be a chemical conjugate of two antibody fragments, such as a conjugate of two Fab fragments or scFv fragments, or combinations thereof. The bispecific antibody is, preferably, human or humanised.

The current invention also relates to a pharmaceutical composition comprising the bispecific antibody according to the invention and a pharmaceutically acceptable carrier. Said bispecific antibody or composition comprising it may be used as a medicament. Said medicament may be useful in the treatment of a congenital, acquired and/or iatrogenic coagulopathy, such as haemophilia A, with or without inhibitors, and haemophilia B, with or without inhibitors.

BRIEF DESCRIPTION OF THE SEQUENCES

Figure 1:
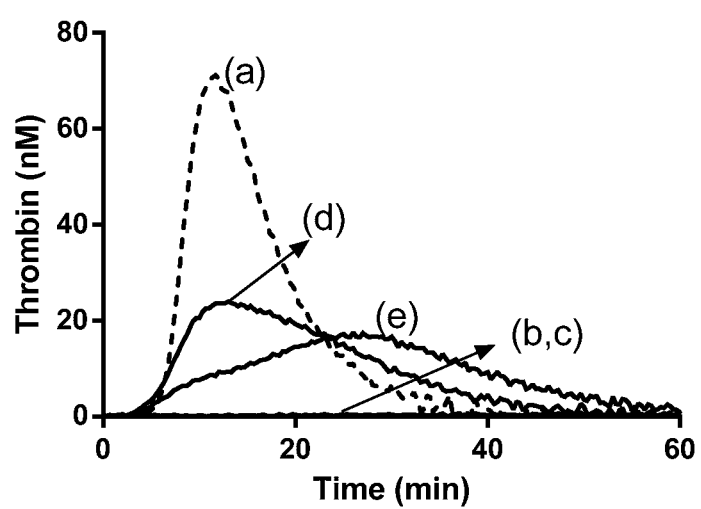
FIG. 1: Thrombin generation is enhanced by certain TFPI (1-79) antibodies and by TFPI KPI-2 antibody mAb 2021 in human plasma under haemophilia A-like conditions with increased TFPI levels. Curve (a) shows the result obtained in normal human plasma without further additions. Curve (b) shows the result when haemophilia A-like conditions are obtained by the addition of 100 µg/ml FVIII antibody (HTI PAHFVIII-S) and 20 nM full-length TFPIα. The suppression of thrombin generation as a result of 20 nM TFPIα in combination with neutralisation of FVIII was not affected by the addition of 200 nM of the TFPI (1-79) antibody mAB 1F91 (c). Addition of 200 nM of the TFPI (1-79) antibody mAb 2F22 (d) and the KPI-2 antibody, mAb 2021 (e), did reverse the thrombin generation but not to a complete restoration to the level obtained in normal human without FVIII antibodies (curve (a)).

SEQ ID NO: 1 represents the amino acid sequence of human TFPI alpha.

SEQ ID NO: 2 represents the amino acid sequence of TFPI (1-161).

SEQ ID NO: 3 represents the amino acid sequence of a tagged TFPI fragment spanning KPI-2.

SEQ ID NO: 4 represents the amino acid sequence of the variable heavy chain of monoclonal antibody (mAb) 2F3.

SEQ ID NO: 5 represents the amino acid sequence of the variable light chain of monoclonal antibody (mAb) 2F3.

SEQ ID NO: 6 represents the amino acid sequence of the variable heavy chain of monoclonal antibody (mAb) 2F22.

SEQ ID NO: 7 represents the amino acid sequence of the variable light chain of monoclonal antibody (mAb) 2F22.

SEQ ID NO: 8 represents the amino acid sequence of the variable heavy chain of monoclonal antibody (mAb) 2F45.

SEQ ID NO: 9 represents the amino acid sequence of the variable light chain of monoclonal antibody (mAb) 2F45.

SEQ ID NO: 10 represents the amino acid sequence of the variable heavy chain of monoclonal antibody (mAb) 1F91

SEQ ID NO: 11 represents the amino acid sequence of the variable light chain of monoclonal antibody (mAb) 1F91.

SEQ ID NO: 12 represents the nucleic acid sequence of the primer used for cloning antibody heavy chains.

SEQ ID NO: 13 represents the nucleic acid sequence of the primer used for cloning antibody light chains.

SEQ ID NO: 14 represents the amino acid sequence of the truncated murine-human chimeric heavy chain of Fab 0296.

SEQ ID NO: 15 represents the amino acid sequence of the murine-human chimeric light chain of monoclonal antibody mAb 0294, Fab 0296, Fab 0295 and mAb 0336.

SEQ ID NO: 16 represents the amino acid sequence of tagged TFPI KPI-1/N-terminal (TFPI (1-79)).

SEQ ID NO: 17 represents the amino acid sequence of the murine-human chimeric heavy chain of monoclonal antibody mAb 0294.

SEQ ID NO: 18 represents the amino acid sequence of the truncated murine-human chimeric heavy chain of Fab 0295.

SEQ ID NO: 19 represents the amino acid sequence of the heavy chain variable domain (VH) of mAb 2021.

SEQ ID NO: 20 represents the amino acid sequence of the light chain variable domain (VL) of mAb 2021.

SEQ ID NO: 21 represents the amino acid sequence of the heavy chain (HC) of Fab 0094.

SEQ ID NO: 22 represents the amino acid sequence of the light chain (LC) of Fab 0094.

SEQ ID NO: 23 represents the amino acid sequence of the heavy chain (HC) of Fab 0088.

SEQ ID NO: 24 represents the amino acid sequence of the light chain (LC) of Fab 0088.

SEQ ID NO: 25 represents the amino acid sequence of the heavy chain (HC) of Fab 0313.

SEQ ID NO: 26 represents the amino acid sequence of the light chain (LC) of Fab 0313.

SEQ ID NO: 27 represents the amino acid sequence of the heavy chain (HC) of mAb 0310.

SEQ ID NO: 28 represents the amino acid sequence of the light chain (LC) of mAb 0310

SEQ ID NO: 29 represents the amino acid sequence of the heavy chain (HC) of mAb 0336.

DESCRIPTION

In vivo, tissue factor pathway inhibitor (TFPI) is found in several compartments. A major fraction of TFPI is associated with the vascular endothelium and a minor fraction circulates in the blood. Two splice variants of TFPI, TFPI alpha (TFPIα) and TFPI beta (TFPIβ) have been described in humans. TFPIβ is presumably the predominant form expressed on the endothelial cell surface, whereas intracellular stores of TFPIα can be released into the circulation upon certain stimuli. TFPIα circulates in the blood as either full-length or truncated protein, associated with lipoproteins or in platelets.

Mature human TFPIα is a 276 amino acid protein (SEQ ID NO: 1) composed of an acidic N-terminal region, three tandemly arranged Kunitz-type inhibitor domains (KPI-1, KPI-2 and KPI-3) interspersed by linker regions and a basic C-terminal tail. The KPI-1, KPI-2 and KPI-3 domains are defined as residues 26-76, residues 97-147 and residues 189-239, respectively, of SEQ ID NO: 1. Mature human TFPIβ is a 193 amino acid protein covalently attached to the endothelial cell surface via a glycosylphosphatidylinositol (GPI)-anchor. The first 161 amino acids of TFPIβ are identical to TFPIα (corresponding to residues 1-161 of SEQ ID NO: 1) whereas the final 12 amino acid of the C-terminal sequence is unrelated to TFPIα and has a GPI-anchor attached to residue 193.

The present invention relates to bispecific antibodies that bind two distinct and/or unique epitopes within residues 1-161 of TFPI. Two monospecific antibodies, each with a unique antigen recognition site, form the basis of the antigen binding fragments, or "arms", of the bispecific antibody of the current invention. The first antigen binding fragment (or "arm") of the bispecific antibody is directed toward an epitope within amino acid residues 1-96 of SEQ ID NO: 1; that is, to an epitope that is within the region encompassing the N-terminal, the KPI-1 domain (residues 26-76 of SEQ ID NO: 1) and the linker region between the KPI-1 and KPI-2 domains. Said epitope is preferably within the region encompassing amino acids 1-76 of TFPI. The second antigen binding fragments (or "arm") of the bispecific antibody is directed toward an epitope within amino acids 77-161 of SEQ ID NO:1, that is, the region of TFPI encompassing the linker region between KPI-1 and KPI-2, the KPI-2 domain and the linker region between KPI-2 and KPI-3. Said epitope is preferably within the KPI-2 domain of TFPI (residues 97-147 of SEQ ID NO: 1).

A single arm of the bispecific antibody, capable of binding within amino acids 77-161 of SEQ ID NO:1, such as within the KPI-2 domain, may in itself, like a monospecific antibody, be incapable of significantly preventing the inhibitory activity of TFPI. It may, however, contribute more significantly to specific blockage of TFPI inhibition when the other arm of the bispecific antibody is bound to the region encompassing amino acids 1-76 of TFPI, such as the KPI-1 domain of TFPI, and vice versa.

Preferably, the dominating binding mode for bispecific KPI-1/KPI-2 binding antibodies as disclosed herein is intramolecular, that is where the two arms of the bispecific KPI-1/KPI-2 binding antibody bind to a single TFPI molecule rather than intermolecular, that is where the two arms of the bispecific KPI-1/KPI-2 binding antibody binds to different TFPI molecules. Intramolecular binding leads to a 1:1 TFPI antibody-complex, whereas an intermolecular binding mode may led to the undesirable formation of larger assemblies of TFPI and bispecific antibody. An intramolecular binding mode may be stimulated by reducing the affinity of one of the antibody arms such as the KPI-1 binding arm.

The bispecific antibody of the invention may have a superior profile when its pro-coagulant effect is compared to the anticipated additive effect of the monospecific antibodies from which it derives. For example, the bispecific antibody may be capable of blocking all inhibitory functions of TFPI, even when the concentration of TFPI is elevated relative to, e.g. normal physiological levels. Linkage of two antigen binding fragments directed towards two separate epitopes of the invention, to obtain a bispecific antibody, such as a Fab-Fab conjugate (herein also referred to as a BiFab), may, due to an avidity effect, lead to a more potent neutralisation of the TFPI activity than that obtained by the combined effect of the two separate antigen binding moieties.

A bispecific antibody of the invention may be capable of modulating the activity of all pools of TFPI.

The term "TFPI" as used herein encompasses naturally occurring forms of tissue factor pathway inhibitor (TFPI) that may be derived from any suitable organism. For example, TFPI for use as described herein may be a mammalian TFPI, such as human, mouse, rat, primate, bovine, ovine, rabbit or porcine TFPI. Preferably the TFPI is human TFPI. The TFPI may be a mature form of TFPI such as a TFPI protein that has undergone post-translational processing within a suitable cell. Such a mature TFPI protein may, for example, be glycosylated. The TFPI may be a full length TFPI protein. The term TFPI also encompasses variants, isoforms and other homologs of such TFPI molecules. TFPI activity refers to its inhibitory activity. Variant TFPI molecules will generally be characterised by having the same type of activity as naturally occurring TFPI, such as the ability to neutralise the catalytic activity of FXa, or the ability to inhibit a complex of TF-FVIIa/FXa.

The term "antibody" herein refers to a protein, derived from an immunoglobulin sequence, which is capable of specifically binding to an antigen or a portion thereof. The term antibody includes, but is not limited to, full length antibodies of any class (or isotype), that is, IgA, IgD, IgE, IgG, IgM and/or IgY. The term may also include one or more antigen-binding fragments of full length antibodies. An antibody that specifically binds to an antigen, or portion thereof, may bind exclusively to that antigen, or a portion thereof, or it may bind to a limited number of homologous antigens, or portions thereof.

Natural full-length antibodies usually comprise at least four polypeptide chains: two heavy (H) chains and two light (L) chains that are connected by disulfide bonds. In some cases, natural antibodies comprise less than four chains, as in the case of the heavy chain only antibodies found in camelids ($V_H$H fragments) and the IgNARs found in Chondrichthyes. One class of immunoglobulins of particular pharmaceutical interest is the IgGs. In humans, the IgG class may be sub-divided into four sub-classes: IgG1, IgG2, IgG3 and IgG4, based on the sequence of their heavy chain constant regions. The light chains can be divided into two types, kappa and lambda chains based on differences in their sequence composition. IgG molecules are composed of two heavy chains, interlinked by two or more disulfide bonds, and two light chains, each attached to a heavy chain by a disulfide bond. An IgG heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs) or hypervariable regions (HvRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The variable domains with the hypervariable regions of the heavy and light chains form a domain that is capable of interacting with an antigen, whilst the constant region of an antibody may mediate binding of the immunoglobulin to host tissues or factors, including, but not limited to various cells of the immune system (effector cells), Fc receptors and the first component (C1q) of the C1 complex of the classical complement system.

The term "monospecific antibody", as used herein, refers to an antibody that has a single antigen recognition site (i.e., is monovalent) or two identical antigen recognition sites (i.e., is bivalent), each of which are specific for one common target antigen.

Monospecific antibodies of the invention may be monoclonal antibodies, in the sense that they represent a set of unique heavy and light chain variable domain sequences as expressed from a single B-cell or by a clonal population of B cells. Antibodies of the invention may be produced and purified using various methods that are known to the person skilled in the art. For example, antibodies may be produced from hybridoma cells. Antibodies may be produced by B-cell expansion. Antibodies or fragments thereof may be recombinantly expressed in mammalian or microbial expression systems, or by in vitro translation. Antibodies or fragments thereof may also be recombinantly expressed as cell surface bound molecules, by means of e.g. phage display, bacterial display, yeast display, mammalian cell display or ribosome or mRNA display. Once produced, antibodies may be screened for their ability to bind TFPI (1-161), full length TFPIα and TFPIβ, such as human TFPI (1-161), full length human TFPIα and human TFPIβ.

Antigen-binding fragments of antibodies may also be monospecific antibodies according to the current invention, as it has been shown that the antigen-binding function of an antibody can be performed by fragments of a full-length antibody. The term "antigen-binding fragment" of an antibody refers to one or more fragment(s) of an antibody that retain(s) the ability to specifically bind to or recognise an antigen, such as TFPIα, such as human TFPIα (SEQ ID NO: 1), such as human TFPI (1-161) (SEQ ID NO:2), such as a human TFPI KPI-2 construct (SEQ ID NO: 3), or another target molecule, as described herein. Examples of antigen-binding fragments include Fab, Fab', Fab$_2$, Fab'$_2$, FabS, Fv (typically the VL and VH domains of a single arm of an antibody), single-chain Fv (scFv; see e.g. Bird et al., *Science* (1988) 242:42S-426; and Huston et al. *PNAS* (1988) 85: 5879-5883), dsFv, Fd (typically the VH and CH1 domain), and dAb (typically a VH domain) fragments; VH, VL, VhH, and V-NAR domains as such; monovalent molecules comprising a single VH and a single VL chain; minibodies, diabodies, triabodies, tetrabodies, and kappa bodies (see, e.g., Ill et al. *Protein Eng* (1997) 10:949-57); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol (2005) 23:1126-1136; WO2005040219, and published U.S. Patent Applications 20050238646 and 20020161201. These antibody fragments may be obtained using conventional techniques known to those of skill in the art, and the fragments may be screened for utility in the same manner as intact antibodies.

"Fab fragments" of an antibody, including "Fab", "Fab'", and "Fab'$_2$" fragments, can be derived from said antibody by cleavage of the heavy chain in the hinge region on the N-terminal or C-terminal side of the hinge cysteine residues connecting the heavy chains of the antibody. A "Fab" fragment includes the variable and constant domains of the light chain and the variable domain and the first constant domain (CH1) of the heavy chain. "Fab'$_2$" fragments comprise a pair of "Fab'" fragments that are generally covalently linked by their hinge cysteines. A Fab' is formally derived from a Fab'$_2$ fragment by cleavage of the hinge disulfide bonds connecting the heavy chains in the Fab'$_2$. Other chemical couplings than disulfide linkages of antibody fragments are also known in the art. A Fab fragment retains the ability of the parent antibody to bind to its antigen, potentially with a lower affinity. Fab'$_2$ fragments are capable of divalent binding, whereas Fab and Fab' fragments can bind monovalently. Generally, Fab fragments lack the constant CH2 and CH3 domains, i.e. the Fc part, where interaction with the Fc receptors would occur. Thus, Fab fragments are in general devoid of effector functions. Fab fragments may be produced by methods known in the art, either by enzymatic cleavage of an antibody, e.g. using papain to obtain the Fab or pepsin to obtain the Fab'$_2$, Fab fragments including Fab, Fab', Fab'$_2$ may be produced recombinantly using techniques that are well known to the person skilled in the art.

An "Fv" fragment is an antibody fragment that contains a complete antigen recognition and binding site, and generally comprises a dimer of one heavy and one light chain variable domain in association that can be covalent in nature, for example in a single chain variable domain fragment (scFv). It is in this configuration that the three hypervariable regions of each variable domain interact to define an antigen-binding site on the surface of the VH-VL dimer. Collectively, the six hypervariable regions or a subset thereof confer antigen-binding specificity to the antibody. However, even a single variable domain comprising only three hypervariable regions specific for an antigen can retain the ability to recognise and bind antigen, although usually at a lower affinity than the entire binding site (Cai & Garen, *Proc. Natl. Acad. Sci. USA* (1996) 93: 6280-6285). For example, naturally occurring camelid antibodies that only have a heavy chain variable domain (VHH) can bind antigen (Desmyter et al., *J. Biol. Chem.* (2002) 277: 23645-23650; Bond et al., *J. Mol. Biol.* (2003) 332: 643-655).

"Single-chain Fv" or "scFv" antibody fragments comprise the VH and VL domains of antibody, where these domains are present in a single polypeptide chain. Generally, the Fv polypeptide further comprises a polypeptide linker between the VH and VL domains that enables the scFv to form the desired structure for antigen-binding. For a review of scFv, see Pluckthun, 1994, In: *The Pharmacology of Monoclonal Antibodies*, Vol. 113, Rosenburg and Moore eds. Springer-Verlag, New York, pp. 269-315.

The term "diabodies" refers to small antibody fragments with two antigen-binding sites, in which fragments comprise a heavy chain variable domain (VH) connected to a light chain variable domain (VL) in the same polypeptide chain (VH and VL). By using a linker that is too short to allow pairing between the two variable domains on the same chain, the variable domains are forced to pair with complementary domains of another chain, creating two antigen-binding sites. Diabodies are described more fully, for example, in EP 404,097; WO 93/11161; and Hollinger et al., 1993, *Proc. Natl. Acad. Sci. USA*, 90:6444-6448.

The expression "linear antibodies" refers to antibodies as described in Zapata et al., 1995, *Protein Eng.*, 8(10):1057-1062. Briefly, these antibodies contain a pair of tandem Fd segments (VH-CH1-VH-CH1) that, together with complementary light chain polypeptides, form a pair of antigen-binding regions. Linear antibodies can be bispecific or monospecific.

Antibody fragments may be obtained using conventional recombinant or protein engineering techniques and the fragments can be screened for binding to TFPI (1-161), full length TFPIα and TFPIβ, or another portion of TFPI, as described herein, in the same manner as intact antibodies.

Antibody fragments of the invention may be made by truncation, e.g. by removal of one or more amino acids from the N and/or C-terminal ends of a polypeptide. Fragments may also be generated by one or more internal deletions.

The term "bispecific antibody" herein refers to an antibody that has two distinct and/or unique antigen recognition sites which enables it to engage two different antigens or two different epitopes on the same antigen. The term "multispecific antibody" refers to an antibody with the ability to engage two or more different antigens or two or more different epitopes on the same antigen. Multispecific antibodies thus comprise bispecific antibodies.

The bispecific antibody of the current invention may be a full length bispecific antibody in IgG format. Bispecific antibodies in full length IgG format, mimicking natural antibodies, can be generated by fusion of two individual hybridomas to form a hybrid quadroma which produces a mixture of antibodies including a fraction of bispecific heterodimerising antibodies (Chelius D. et al.; *MAbs.* 2010 May-June; 2(3): 309-319). Bispecific heterodimerising antibodies may alternatively be produced by using recombinant technologies. Heterodimerisation can be also be achieved by engineering the dimerisation interface of the Fc region to promote heterodimerisation. One example hereof is the so-called knob-in-hole mutations where sterically bulky side chains (knobs) are introduced in one Fc matched by sterically small side chains (holes) on the opposite Fc thereby creating steric complementarity promoting heterodimerisation. Other methods for engineered heterodimerisation Fc interfaces are electrostatic complementarity, fusion to non-IgG heterodimerisation domains or utilising the natural Fab-arm exchange phenomenon of human IgG4 to control heterodimerisation. Examples of heterodimerised bispecific antibodies are well described in the literature, e.g. (Klein C, et al.; *MAbs.* 2012 November-December; 4(6): 653-663).

Special attention has to be paid to the light chains in heterodimeric antibodies. Correct pairing of LCs and HCs can be accomplished by the use of a common light chain. Again engineering of the LC/HC interface can be used to promote heterodimerisation or light chain cross-over engineering as in CrossMabs. In vitro re-assembly under mildly reducing conditions of antibodies from two individual IgGs containing appropriate mutations can also be used to generate bispecifics (e.g. Labrijn et al., *PNAS,* 110, 5145-5150 (2013)). Also the natural Fab-arm exchange method is reported to ensure correct light chains paring.

Multispecific antibody-based molecules may also be expressed recombinantly as fusion proteins combining the natural modules of IgGs to form multispecific and multivalent antibody derivatives as described in the literature. Examples of fusion antibodies are DVD-Igs, IgG-scFV, Diabodies, DARTs etc (Kontermann, *MAbs.* 2012 March-April 4(2): 182-197). Specific detection or purification tags, half-life extension moieties or other components can be incorporated in the fusion proteins. Additional non-IgG modalities may also be incorporated in the fusion proteins. Bispecific full length antibodies based on FC heterodimerisation are commonly referred to as asymmetric IgGs, irrespective of the LC paring methodology.

Multispecific antibody-based molecules may also be produced by chemical conjugation or coupling of individual full length IgGs or coupling of fragments of IgGs to form multispecific and multivalent antibody derivatives as described in the literature. Examples of fusion antibodies are chemical coupled Fab'$_2$, IgG-dimer etc. (Kontermann, *MAbs.* 2012 March-April 4(2): 182-197). Specific detection or purification tags, half-life extension molecules or other components can be incorporated in the conjugate proteins. Additional non-IgG polypeptide may also be incorporated in the fusion proteins. An example of such a bispecific antibody is provided in the examples.

Multispecific molecules may also be produced by combining recombinant and chemical methods including those described above.

The bispecific antibody of the current invention may be a chemical conjugate of two antigen binding fragments, such as a conjugate of two Fab fragments (a BiFab) or two scFv fragments. Bispecific antibodies or two monospecific antibodies that bind two unique epitopes on TFPI may be generated by methods known to a person skilled in the art. Bispecific formats may be prepared, for example, by chemical conjugation of two antibody fragments—such as two Fab or scFv fragments—either directly or via a linker providing the required flexibility for proper function. One specific method for coupling Fab fragments is to use the thiol functionality in cysteine residues placed appropriately in the Fab fragments.

Bispecific, or bifunctional, antibodies of the invention may be obtained by chemical conjugation of two antibodies or fragments thereof (that bind to different epitopes of TFPI), as described in *J Immunol* 1987; 139:2367-2375 or *J Immunol* 2001; 166:1320-1326, or as described in the following:

mAb1 (or fragment)-mAb2 (or fragment)

mAb1 (or fragment)-linker-mAb2 (or fragment)

The linkage can be a single covalent bond (direct linkage) or comprise a biradical generally described as:

wherein X is at least, but not limited to, one atom selected from the group consisting of carbon, oxygen, sulfur, phosphor, and nitrogen. * shows the positions of connections of this biradical. The term "biradical" refers to an even-electron chemical compound with two free radical centers which act independently of one another.

In one embodiment the linker is a chain composed of no more than 40 atoms.

In one embodiment, a chemical moiety used in the linker comprises the biradical with the structure

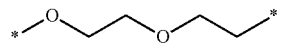 [SMILES: *CCOCCO*]

In one embodiment, the linker part comprises the biradical which has a symmetrical structure (homo-bifunctionalised linker).

The linker may also be a polymer of a structure which is similar to the description above.

In an embodiment, a chemical moiety used in the linker comprises a polymer: a macromolecule composed of two or more repeating structural units that are connected by covalent chemical bonds. Such a polymer may be hydrophilic.

The term hydrophilic or "water-soluble" refers to moieties that have some detectable degree of solubility in water. Methods to detect and/or quantify water solubility are well known in the art.

Exemplary water-soluble polymers according to the invention include peptides, saccharides, (poly)ethers, (poly)amines, (poly)carboxylic acids and the like. Peptides can have mixed sequences or can be composed of a single amino acid, e.g., (poly)lysine. An exemplary polysaccharide is (poly)sialic acid. An exemplary (poly)ether is (poly)ethylene glycol. (Poly)ethylene imine is an exemplary polyamine, and (poly)acrylic acid is a representative (poly)carboxylic acid.

Many other polymers are also suitable for the invention. Polymer backbones that are water-soluble are particularly useful in the invention. Examples of suitable polymers include, but are not limited to, other poly(alkylene glycols), such as poly(propylene glycol) ("PPG"), copolymers of ethylene glycol and propylene glycol and the like, poly (oxyethylated polyol), poly(vinylpyrrolidone), poly(hydroxypropylmethacrylamide), poly([alpha]-hydroxy acid), poly(vinyl alcohol), polyphosphazene, polyoxazoline, poly (N-acryloylmorpholine), such as described in U.S. Pat. No. 5,629,384, which is incorporated by reference herein in its entirety, as well as copolymers, terpolymers, and mixtures thereof.

The polymeric linker is, preferably, linear.

Although the molecular weight of each individual polymer chain may vary, the average molecular weight of the polymer is typically in the range of from about 1000 Da (1 kDa) to about 40,000 Da (40 kDa), such as about 1000 Da to about 12,000 Da such as about 2,000 Da to about 11,000 Da, such as about 2000 Da to about 3,000 Da; about 3000 Da to about 4,000 Da; about 4000 to about 5,000 Da; about 5000 to about 6,000 Da; about 6,000 to about 7,000 Da; about 7,000 to about 8,000 Da; about 8,000 to about 9,000 Da; about 9,000 to about 10,000 Da; or about 10,000 to about 11,000 Da. It should be understood that these sizes represent estimates rather than exact measures. According to a preferred embodiment, the molecules according to the invention are conjugated with a heterogeneous population of hydrophilic polymers.

In a particular embodiment, a chemical moiety used in the linker comprises polyethylene glycol (PEG).

The term "PEG" herein refers to a biradical comprising the structure

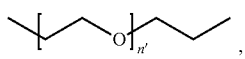

wherein n' is an integer larger than 1.

PEG is prepared by polymerisation of ethylene oxide and is commercially available over a wide range of molecular weights. The PEG for use according to the present invention is, preferably, linear.

Furthermore, "PEG" may refer to a polyethylene glycol compound, or derivative thereof, with or without coupling agents, coupling or activating moieties (e.g., with carboxylic acid/active ester, keto, alkoxyamine, thiol, triflate, tresylate, aziridine, oxirane, alkyne, azide or a maleimide moiety). The other linkers mentioned herein may also be with or without coupling agents, coupling or activating moieties (e.g., with carboxylic acid/active ester, keto, alkoxyamine, thiol, triflate, tresylate, aziridine, oxirane, alkyne, azide or a maleimide moiety) In one particular embodiment the PEG for use according to the invention is monodisperse. In another particular embodiment, the PEG for use according to the invention is polydisperse.

Polydisperse PEG is composed of PEG molecules that have various molecular weights. The size distribution can be characterised statistically by its weight average molecular weight (Mw) and its number average molecular weight (Mn), the ratio of which is called the polydispersity index (Mw/Mn) (see e.g. "Polymer Synthesis and Characterization", J. A. Nairn, University of Utah, 2003). Mw and Mn can be measured by mass spectroscopy.

The polydispersity index may be a number that is greater than or equal to one and it may be estimated from Gel Permeation Chromatographic data. When the polydispersity index is 1, the product is monodisperse and is thus made up of compounds with a single molecular weight. When the polydispersity index is greater than 1 the polymer is polydisperse, and the polydispersity index tells how broad the distribution of polymers with different molecular weights is. The polydispersity index typically increases with the molecular weight of the PEG. In particular embodiments, the polydispersity index of the PEG for use according to the invention is i) below 1.06, ii) below 1.05, iii) below 1.04, iv) below 1.03 or v) between 1.02 and 1.03.

Different forms of PEG are available, depending on the initiator used for the polymerisation process.

Numerous methods for conjugation of PEG substituents are described in *Advanced Drug Delivery Reviews*, 2002, 54, 459-476, *Nature Reviews Drug Discovery*, 2003, 2, 214-221 DOI:10.1038/nrd1033, *Adv Polym Sci*, 2006, 192, 95-134, DOI 10.1007/12_022, Springer-Verlag, Berlin Heidelberg, 2005, and references therein. Alternatively, conjugation of the hydrophilic polymer substituent could take place by use of enzymatic methods. Such methods are for instance use of transglutaminases as described in WO2006134148.

To effect covalent attachment of the polymer molecule(s) to the polypeptide, the end groups of the polymer molecule are provided in activated form, i.e. with reactive functional groups. Suitable activated polymer molecules are commercially available, e.g. from Sigma-Aldrich Corporation, St. Louis, Mo., USA, Rapp Polymere GmbH, Tübingen, Germany, or from PolyMASC Pharmaceuticals plc, UK. Alternatively, the polymer molecules can be activated by conventional methods known in the art, e.g. as disclosed in WO 90/13540. Specific examples of activated PEG polymers are disclosed in U.S. Pat. Nos. 5,932,462 and 5,643,575. Furthermore, the following publications disclose useful polymer molecules and/or PEGylation chemistries: WO2003/031464, WO2004/099231.

The conjugation of the monoclonal antibody, or fragment thereof, with the activated polymer molecules may be conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y., Bioconjugate Techniques, Second Edition, Greg T. Hermanson, 2008, Amsterdam, Elsevier). The skilled person would be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfhydryl, succinimidyl, maleimide, vinylsulfone or haloacetate). The PEGylation may be directed towards conjugation to available attachment groups on the polypeptide (i.e. such attachment groups that are exposed at the surface of the polypeptide) or may be directed towards one or more specific attachment groups, e.g. the N-terminal amino group or a thiol. Furthermore, the conjugation may be achieved in one step or in a stepwise manner.

In another embodiment, a chemical moiety used as the linker is hydroxyethyl starch. The term "hydroxyethyl starch" (HES/HAES), as used herein, refers to a nonionic starch derivative. Different types of hydroxyethyl starches are typically described by their average molecular weight, typically around 130 to 200 kDa.

In another embodiment, a chemical moiety used in the linker comprises polysialic acid.

In another embodiment, a chemical moiety used in the linker comprises heparosan polymer which is described in for instance *Glycobiology* (2011) 21: 1331-1340.

In another embodiment, a chemical moiety in the linker is used to attach at least one of the proteins to a glycan: a polysaccharide or an oligosaccharide that is attached to a protein.

In another embodiment, a chemical moiety in the linker is used to attach at least one of the proteins to an O-linked glycan.

In another embodiment, a chemical moiety in the linker is used to attach at least one of the proteins to an N-linked glycan.

Both N-glycans and O-glycans are attached to proteins such as antibodies by the cells producing these proteins. The cellular N-glycosylation machinery recognises and glycosylates N-glycosylation signals (N—X—S/T motifs) in the amino acid chain, as the nascent protein is translocated from the ribosome to the endoplasmic reticulum (Kiely et al., *J. Biol. Chem.* 1976, 251: 5490; Glabe et al., *J. Biol. Chem.*, 1980, 255, 9236). Likewise, 0-glycans are attached to specific O-glycosylation sites in the amino acid chain, but the motifs triggering O-glycosylation are much more heterogeneous than the N-glycosylation signals, and our ability to predict O-glycosylation sites in amino acid sequences is still inadequate (Julenius et al., *Glycobiology*, 2005, 15: 153). Methods of conjugating polypeptides with various polymeric side groups are described e.g. in WO0331464.

In another embodiment, a chemical moiety used in the linker comprises a chemical moiety, which is used to attach said linker to at least one of the proteins with a structure selected of the biradicals:

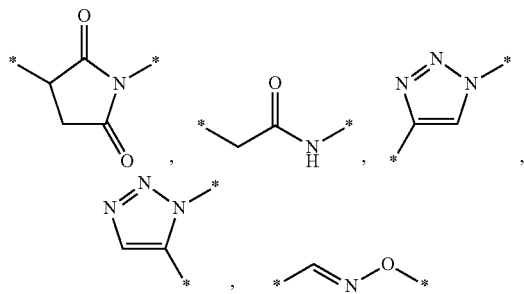

Bispecific antibodies of the current invention may be human, humanised, chimeric or engineered antibodies.

The term "human antibody", as used herein, is intended to include antibodies having variable regions in which at least a portion of a framework region and/or at least a portion of a CDR region are derived from human germline immunoglobulin sequences. (For example, a human antibody may have variable regions in which both the framework and CDR regions are derived from human germline immunoglobulin sequences.) Furthermore, if the antibody contains a constant region, the constant region or a portion thereof is also derived from human germline immunoglobulin sequences.

The human antibodies of the invention may include amino acid residues not encoded by human germline immunoglobulin sequences (e.g., mutations introduced by random or site-specific mutagenesis in vitro or by somatic mutation in vivo).

Such a human bispecific antibody may be derived from two human monoclonal antibodies. A human monoclonal antibody may be produced by a hybridoma which includes a B cell obtained from a transgenic nonhuman animal, e.g., a transgenic mouse, having a genome comprising human immunoglobulin heavy and light chain gene segments repertoires, fused to an immortalised cell.

Human antibodies may be isolated from sequence libraries built on selections of human germline sequences, further diversified with natural and synthetic sequence diversity.

Human antibodies may be prepared by in vitro immunisation of human lymphocytes followed by transformation of the lymphocytes with Epstein-Barr virus.

The term "human antibody derivative" refers to any modified form of the human antibody, such as a conjugate of the antibody and another agent or antibody.

The term "humanised antibody", as used herein, refers to a human/non-human chimeric antibody that contains sequence elements (CDR regions or parts thereof) derived from a non-human immunoglobulin. A humanised antibody is, thus, a human immunoglobulin (recipient antibody) in which at least residues from a hypervariable region of the recipient are replaced by residues from a hypervariable region of an antibody from a non-human species (donor antibody) such as from a mouse, rat, rabbit or non-human primate, which have the desired specificity, affinity, sequence composition and functionality. In some instances, framework (FR) residues of the human immunoglobulin are replaced by corresponding non-human residues. An example of such a modification is the introduction of one or more so-called back-mutations, which are typically amino acid residues derived from the donor antibody. Humanisation of an antibody may be carried out using recombinant techniques known to the person skilled in the art (see, e.g., Antibody Engineering, Methods in Molecular Biology, vol. 248, edited by Benny K. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanised antibody can be further optimised for e.g. affinity, functionality and biophysical properties by identification of critical framework positions where re-introduction (backmutation) of the amino acid residue from the donor antibody has beneficial impact on the properties of the humanised antibody. In addition to donor antibody derived backmutations, the humanised antibody can be engineered by introduction of germline residues in the CDR or framework regions, elimination of immunogenic epitopes, site-directed mutagenesis, affinity maturation, etc.

Furthermore, humanised antibodies may comprise residues that are not found in the recipient antibody or in the donor antibody. These modifications are made to further refine antibody performance. In general, a humanised antibody will comprise at least one—typically two—variable domains, in which all or substantially all of the CDR regions correspond to those of a non-human immunoglobulin and in which all or substantially all of the FR residues are those of a human immunoglobulin sequence. The humanised antibody can, optionally, also comprise at least a portion of an immunoglobulin constant region (Fc), typically that of a human immunoglobulin.

The term "humanised antibody derivative" refers to any modified form of the humanised antibody, such as a conjugate of the antibody and another chemical agent or antibody or antibody fragment or polypeptide.

The term "chimeric antibody", as used herein, refers to an antibody whose light and heavy chain genes have been constructed, typically by genetic engineering, from immunoglobulin variable and constant region genes that originate from different species. For example, the variable segments of genes from a mouse monoclonal antibody may be joined to human constant regions.

The fragment crystallisable region ("Fc region"/"Fc domain") of an antibody is the C-terminal region of an antibody, which comprises the constant CH2 and CH3 domains. The Fc domain may interact with cell surface receptors called Fc receptors, as well as some proteins of the complement system. The Fc region enables antibodies to interact with the immune system. In one aspect of the invention, antibodies may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others. Furthermore, an antibody of the invention may be chemically modified (e.g., one or more chemical moieties can be attached to the antibody) or be modified to alter its glycosylation, again to alter one or more functional properties of the antibody. An IgG1 antibody may carry a modified Fc domain comprising one or more, and perhaps all of the following mutations that will result in decreased affinity to certain Fc receptors (L234A, L235E, and G237A) and in reduced C1q-mediated complement fixation (A330S and P331S), respectively (residue numbering according to the EU index).

The isotype of an antibody of the invention may be IgG, such as IgG1, such as IgG2, such as IgG4. If desired, the class of an antibody may be "switched" by known techniques. For example, an antibody that was originally produced as an IgM molecule may be class switched to an IgG antibody. Class switching techniques also may be used to convert one IgG subclass to another, for example: from IgG1 to IgG2 or IgG4; from IgG2 to IgG1 or IgG4; or from IgG4 to IgG1 or IgG2. Engineering of antibodies to generate constant region chimeric molecules, by combination of regions from different IgG subclasses, can also be performed.

In one embodiment, the hinge region of CH1 is modified such that the number of cysteine residues in the hinge region is altered, e.g., increased or decreased. This approach is described further for instance in U.S. Pat. No. 5,677,425 by Bodmer et al.

The constant region may be modified to stabilise the antibody, e.g., to reduce the risk of a bivalent antibody separating into two monovalent VH-VL fragments. For example, in an IgG4 constant region, residue S228 (according to the EU numbering index, S241 according to Kabat) may be mutated to a proline (P) residue to stabilise inter heavy chain disulphide bridge formation at the hinge (see, e.g., Angal et al., *Mol Immunol.* 1993; 30:105-8).

A bispecific antibody of the current invention may comprise an antigen-binding fragment, or variant thereof, of the mAb 2F3 antibody; the mAb 2F22 antibody (such as Fab 0295 or Fab 0296); the mAb 2F45 antibody; or the mAb 1F91 antibody.

A bispecific antibody of the current invention may further comprise an antigen-binding fragment, or variant thereof, of the mAb 2021 antibody, a humanised monoclonal antibody that was first described in WO2010/072691 and which is hereby incorporated by reference. Examples of such antigen binding fragments, or variants thereof, include Fab 0088, Fab 0094 or Fab 0313, as described herein. The monoclonal, murine antibody from which mAb 2021 is derived may be produced as described in WO2010/072691.

Any one of the above-mentioned bispecific antibodies, comprising an antigen binding fragment, or variant thereof, of mAb 2F3, mAb 2F22, mAb 2F45 or mAb 1F91 and an antigen binding fragment, or variant thereof, of mAb 2021, may be a full length bispecific antibody in IgG format or a bispecific molecule composed of antibody fragments. Antibodies or fragments thereof may be defined in terms of their complementarity-determining regions (CDRs). The term "complementarity-determining region" or "hypervariable region", when used herein, refers to the regions of an antibody in which amino acid residues involved in antigen-binding are situated. The region of hypervariability or CDRs can be identified as the regions with the highest variability in amino acid alignments of antibody variable domains. Databases can be used for CDR identification such as the Kabat database, the CDRs e.g. being defined as comprising amino acid residues 24-34 (L1), 50-56 (L2) and 89-97 (L3) of the light-chain variable domain and 31-35 (H1), 50-65 (H2) and 95-102 (H3) in the heavy-chain variable domain; (Kabat et al., Sequences of Proteins of Immunological Interest, 1991) Sequences of Proteins of Immunological Interest, Fifth Edition, U.S. Department of Health and Human Services, NIH Publication No. 91-3242) Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196: 901-917). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "framework region" or "FR" residues refer to those VH or VL amino acid residues that are not within the CDRs, as defined herein.

An antigen recognition site of the bispecific antibody of the invention may comprise a CDR region from one or more of the specific antibodies or antibody fragments disclosed herein, such as a CDR region from within SEQ ID NOs: 4 to 11, 14 to 15, 17 to 26, as defined according to the sequential amino acid numbering disclosed herein or using Kabat numbering.

The first antigen recognition site of the bispecific antibody may have a heavy chain comprising:
- a CDR1 sequence corresponding to amino acids 31 to 35 of SEQ ID NO: 4 (SYGVH), wherein one of these amino acid residues may be substituted by a different amino acid residue; and/or
- a CDR2 sequence corresponding to amino acids 50 to 65 of SEQ ID NO: 4 (VIWRGGSTDFNAAFMS), wherein one, two or three of these amino acids may be substituted by a different amino acid residue; and/or
- a CDR3 sequence corresponding to amino acids 98 to 110 of SEQ ID NO: 4 (NSHGNYVGYAMDY), wherein one or two of these amino acid residues may be substituted by a different amino acid.

and said first antigen recognition site may have a light chain comprising:
- a CDR1 sequence corresponding to amino acids 24 to 34 (KASENVGAAVA) of SEQ ID NO: 5, wherein one, two or three of these amino acid residues may be substituted by a different amino acid residue; and/or
- a CDR2 sequence corresponding to amino acids 50 to 56 (SASNRYT) of SEQ ID NO: 5, wherein one of these amino acid residues may be substituted by a different amino acid residue; and/or
- a CDR3 sequence corresponding to amino acids 89 to 96 (QQYTNYPT) of SEQ ID NO: 5, wherein one of these amino acid residues may be substituted by a different amino acid residue.

The first antigen recognition site of the bispecific antibody may have a heavy chain comprising:
- a CDR1 sequence corresponding to amino acids 31 to 35 of SEQ ID NO: 6 (NYGVH), wherein one of these amino acid residues may be substituted by a different amino acid residue; and/or
- a CDR2 sequence corresponding to amino acids 50 to 65 of SEQ ID NO: 6 (VIWRGGSIDYNAAFMS), wherein one, two or three of these amino acids may be substituted by a different amino acid residue; and/or
- a CDR3 sequence corresponding to amino acids 98 to 110 of SEQ ID NO: 6 (NSHGNYVGYAMDY), wherein one or two of these amino acid residues may be substituted by a different amino acid.

and said first antigen recognition site may have a light chain comprising:
- a CDR1 sequence corresponding to amino acids 24 to 34 (KASQSVGPAVA) of SEQ ID NO: 7, wherein one, two or three of these amino acid residues may be substituted by a different amino acid residue; and/or
- a CDR2 sequence corresponding to amino acids 50 to 56 (SASNRYT) of SEQ ID NO: 7, wherein one of these amino acid residues may be substituted by a different amino acid residue; and/or
- a CDR3 sequence corresponding to amino acids 89 to 96 (QQYTSYPT) of SEQ ID NO: 7, wherein one of these amino acid residues may be substituted by a different amino acid residue.

The first antigen recognition site of the bispecific antibody may have a heavy chain comprising:
- a CDR1 sequence corresponding to amino acids 31 to 35 of SEQ ID NO: 8 (GYGVH), wherein one of these amino acid residues may be substituted by a different amino acid residue; and/or
- a CDR2 sequence corresponding to amino acids 50 to 65 of SEQ ID NO: 8 (VIWRGGSIDYNAAFMS), wherein one, two or three of these amino acids may be substituted by a different amino acid residue; and/or
- a CDR3 sequence corresponding to amino acids 98 to 110 of SEQ ID NO: 8 (NSHGNYVGYAMDY), wherein one or two of these amino acid residues may be substituted by a different amino acid.

and said first antigen recognition site may have a light chain comprising:
- a CDR1 sequence corresponding to amino acids 24 to 34 (KASQNVGTAVA) of SEQ ID NO: 9, wherein one, two or three of these amino acid residues may be substituted by a different amino acid residue; and/or
- a CDR2 sequence corresponding to amino acids 50 to 56 (SASNRYT) of SEQ ID NO: 9, wherein one of these amino acid residues may be substituted by a different amino acid residue; and/or
- a CDR3 sequence corresponding to amino acids 89 to 96 (QQYTSYPT) of SEQ ID NO: 9, wherein one of these amino acid residues may be substituted by a different amino acid residue.

The first antigen recognition site of the bispecific antibody may have a heavy chain comprising:
- a CDR1 sequence corresponding to amino acids 31 to 36 of SEQ ID NO: 10 (SDYAWN), wherein one of these amino acid residues may be substituted by a different amino acid residue; and/or
- a CDR2 sequence corresponding to amino acids 51 to 66 of SEQ ID NO: 10 (YISYSGSTSYNPSLKS), wherein one, two or three of these amino acids may be substituted by a different amino acid residue; and/or
- a CDR3 sequence corresponding to amino acids 99 to 104 of SEQ ID NO: 10 (WAYDGP), wherein one of these amino acid residues may be substituted by a different amino acid.

and said first antigen recognition site may have a light chain comprising:
- a CDR1 sequence corresponding to amino acids 24 to 33 (RASSSVSHMH) of SEQ ID NO: 11, wherein one or two of these amino acid residues may be substituted by a different amino acid residue; and/or
- a CDR2 sequence corresponding to amino acids 49 to 55 (ATSNLAS) of SEQ ID NO: 11, wherein one of these amino acid residues may be substituted by a different amino acid residue; and/or
- a CDR3 sequence corresponding to amino acids 88 to 96 (QQWSSNPFT) of SEQ ID NO: 11, wherein one of these amino acid residues may be substituted by a different amino acid residue.

The second antigen recognition site of the bispecific antibody may have a heavy chain comprising:
- a CDR1 sequence corresponding to amino acids 31 to 35 (NYAMS) of SEQ ID NO:19, wherein one of these amino acids may be substituted by a different amino acid; and/or
- a CDR2 sequence corresponding to amino acids 50 to 66 of SEQ ID NO:19 (TISRSGSYSYFPDSVQG), SEQ ID NO: 21 TISRSGSYSYYPDSVKG or SEQ ID NO: 25 (TISRSGSYSYYADSVKG) wherein one, two or three of these amino acids may be substituted by a different amino acid; and/or
- a CDR3 sequence corresponding to amino acids 99 to 110 (LGGYDEGDAMDS) of SEQ ID NO:19, wherein one, two or three of these amino acids may be substituted by a different amino acid.

and said second antigen recognition site may have a light chain comprising:

a CDR1 sequence corresponding to amino acids 24 to 39 (KSSQSLLESDGKTYLN) of SEQ ID NO: 20, wherein one, two or three of these amino acids may be substituted with a different amino acid; and/or a CDR2 sequence corresponding to amino acids 55 to 61 (LVSILDS) of SEQ ID NO: 20, wherein one or two of these amino acids may be substituted with a different amino acid; and/or a CDR3 sequence corresponding to amino acids 94 to 102 (LQATHFPQT) of SEQ ID NO: 20, wherein one or two of these amino acids may be substituted with a different amino acid.

Said amino acid substitutions may be conservative substitutions, as described below.

Thus, a TFPI (1-79) specific antibody fragment is combined with a KPI-2 domain specific antibody fragment thereof to form a bispecific antibody in inter alia fusion format, IgG fragment format, full length IgG format or as a Fab-Fab conjugate (BiFab).

In one such embodiment, a Fab fragment carrying the VH and VL regions of mAb 1F91 (SEQ ID NOs: 10, 11) is combined with a Fab fragment carrying the VH, VL regions of mAb 2021 (SEQ ID NOs: 19, 20).

In one such embodiment, a Fab fragment carrying the VH and VL regions of mAb 1F91 (SEQ ID NOs: 10, 11) is combined with Fab fragment 0094 (SEQ ID NOs: 21, 22).

In one such embodiment, a Fab fragment carrying the VH and VL regions of mAb 1F91 (SEQ ID NOs: 10, 11) is combined with Fab fragment 0313 (SEQ ID NOs: 25, 26).

In one such embodiment, a Fab fragment of carrying the VH and VL regions of mAb 2F3 (SEQ ID NOs: 4, 5) is combined with a Fab fragment carrying the VH, VL regions of mAb 2021 (SEQ ID NOs: 19, 20).

In one such embodiment, a Fab fragment carrying the VH and VL regions of mAb 2F3 (SEQ ID NOs: 4, 5) is combined with Fab fragment 0094 (SEQ ID NOs: 21, 22).

In one such embodiment, a Fab fragment carrying the VH and VL regions of mAb 2F3 (SEQ ID NOs: 4, 5) is combined with Fab fragment 0313 (SEQ ID NOs: 25, 26).

In one such embodiment, a Fab fragment carrying the VH and VL regions of mAb 2F22 (SEQ ID NOs: 6, 7) is combined with a Fab fragment carrying the VH, VL regions of mAb 2021 (SEQ ID NOs: 19, 20).

In one such embodiment, a Fab fragment carrying the VH and VL regions of mAb 2F22 (SEQ ID NOs: 6, 7) is combined with Fab fragment 0094 (SEQ ID NOs: 21, 22).

In one such embodiment, a Fab fragment carrying the VH and VL regions of mAb 2F22 (SEQ ID NOs: 6, 7) is combined with Fab fragment 0313 (SEQ ID NOs: 25, 26).

In one such embodiment, a Fab fragment carrying the VH, VL regions of mAb 2F45 (SEQ ID NOs: 8, 9) is combined with a Fab fragment of mAb 2021 (SEQ ID NOs: 19, 20).

In one such embodiment, a Fab fragment carrying the VH and VL regions of mAb 2F45 (SEQ ID NOs: 8, 9) is combined with Fab fragment 0094 (SEQ ID NOs: 21, 22).

In one such embodiment, a Fab fragment carrying the VH and VL regions of mAb 2F45 (SEQ ID NOs: 8, 9) is combined with Fab fragment 0313 (SEQ ID NOs: 25, 26).

One Fab-Fab conjugate (BiFab) according to the current invention may be BiFab 9041 (Fab 0088 (SEQ ID NOs: 23, 24) conjugated to Fab 0295 (SEQ ID NOs: 15, 18).

Another Fab-Fab conjugate (BiFab) according to the current invention may be BiFab 9042, that is Fab 0313 (SEQ ID NOs: 25, 26) conjugated to Fab 0295 (SEQ ID NOs: 15,18).

In one embodiment a bispecific antibody in full length format (mAb 0421) consists of individual arms from mAb 0310 (SEQ ID NOs: 27, 28) and mAb 0336 (SEQ ID NOs: 15, 29). A variant antibody may comprise 1, 2, 3, 4, 5, up to 10 or more amino acid substitutions and/or deletions and/or insertions from the specific sequences and fragments discussed above. "Deletion" variants may comprise the deletion of individual amino acids, deletion of small groups of amino acids such as 1, 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 1, 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid which appears in the sequence is a structural analogue thereof. Amino acids used in the sequences may also be derivatized or modified, e.g. labelled, providing the function of the antibody is not significantly adversely affected.

Substitutions may be, but are not limited to, conservative substitutions.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogues thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. For example, a polynucleotide of the invention may encode a polypeptide comprising the sequence of any one of SEQ ID NOs: 4-11, 14-15 or 17-26, as described above. A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide encoding a polypeptide of the present invention preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example, the UWGCG Package provides the BESTFIT program which can be used to calculate homology (e.g. used on its default settings) (Devereux et al. (1984) *Nucleic Acids Research* 12: 387-395).

The PILEUP and BLAST algorithms can also be used to calculate homology or line up sequences (typically on their default settings), for example as described in Altschul S. F. (1993) *J Mol Evol* 36: 290-300; Altschul, S. F. et al. (1990) *J Mol Biol* 215: 403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al. supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787.

The term "antigen" (Ag) herein refers to the entity used for immunisation of an immunocompetent vertebrate to produce an antibody (Ab) that recognises the Ag. In the context of the current invention, suitable antigens include human TFPI (1-161) and full length human TFPIα. Herein, Ag is termed more broadly and is generally intended to include target molecules that are specifically recognised by the Ab, thus including fragments or mimics of the molecule used in the immunisation process, or other process, e.g. phage display, used for generating the Ab.

The term "epitope", as used herein, is defined in the context of a molecular interaction between an "antigen-binding polypeptide", such as an antibody (Ab), and its corresponding antigen (Ag). Generally, "epitope" refers to the area or region on an Ag to which an Ab specifically binds, i.e. the area or region in physical contact with the Ab. Physical contact may be defined using various criteria (e.g. a distance cut-off of 2-6 Å, such as 3 Å, such as 4 Å, such as 5 Å; or solvent accessibility) for atoms in the Ab and Ag molecules. A protein epitope may comprise amino acid residues in the Ag that are directly involved in binding to a Ab (also called the immunodominant component of the epitope) and other amino acid residues, which are not directly involved in binding, such as amino acid residues of the Ag which are effectively blocked by the Ab, i.e. amino acid residues within the "solvent-excluded surface" and/or the "footprint" of the Ab.

The term "epitope" herein comprises both types of binding region in any particular region of TFPI that specifically binds to a mono- or bispecific TFPI antibody, or another TFPI-specific agent according to the invention, unless otherwise stated. TFPI may comprise a number of different epitopes, which may include, without limitation, (1) linear peptide epitopes (2) conformational epitopes which consist of one or more non-contiguous amino acids located near each other in the mature TFPI conformation; and (3) post-translational epitopes which consist, either in whole or part, of molecular structures covalently attached to TFPI, such as carbohydrate groups.

The epitope for a given antibody (Ab)/antigen (Ag) pair can be described and characterised at different levels of detail using a variety of experimental and computational epitope mapping methods. The experimental methods include mutagenesis, X-ray crystallography, Nuclear Magnetic Resonance (NMR) spectroscopy, Hydrogen deuterium eXchange Mass Spectrometry (HX-MS) and various competition binding methods; methods that are known in the art. As each method relies on a unique principle, the description of an epitope is intimately linked to the method by which it has been determined. Thus, depending on the epitope mapping method employed, the epitope for a given Ab/Ag pair may be described differently.

At its most detailed level, the epitope for the interaction between the Ag and the Ab can be described by the spatial coordinates defining the atomic contacts present in the Ag-Ab interaction, as well as information about their relative contributions to the binding thermodynamics. At a less detailed level, the epitope can be characterised by the spatial coordinates defining the atomic contacts between the Ag and Ab. At an even less detailed level the epitope can be characterised by the amino acid residues that it comprises as defined by a specific criteria such as the distance between or solvent accessibility of atoms in the Ab:Ag complex. At a further less detailed level the epitope can be characterised through function, e.g. by competition binding with other Abs. The epitope can also be defined more generically as comprising amino acid residues for which substitution by another amino acid will alter the characteristics of the interaction between the Ab and Ag.

In the context of an X-ray derived crystal structure defined by spatial coordinates of a complex between an Ab, e.g. a Fab fragment, and its Ag, the term epitope is herein, unless otherwise specified or contradicted by context, specifically defined as being TFPI residues having a heavy atom (i.e. a non-hydrogen atom) within a distance of 4 Å from a heavy atom in the Ab.

From the fact that descriptions and definitions of epitopes, dependent on the epitope mapping method used, are obtained at different levels of detail, it follows that comparison of epitopes for different Abs on the same Ag can similarly be conducted at different levels of detail.

Epitopes described at the amino acid level, e.g. determined from an X-ray structure, are said to be identical if they contain the same set of amino acid residues. Epitopes are said to overlap if at least one amino acid is shared by the epitopes. Epitopes are said to be separate (unique) if no amino acid residue is shared by the epitopes.

The definition of the term "paratope" is derived from the above definition of "epitope" by reversing the perspective. Thus, the term "paratope" refers to the area or region on the Ab to which an Ag specifically binds, i.e. with which it makes physical contact to the Ag.

In the context of an X-ray derived crystal structure, defined by spatial coordinates of a complex between an Ab, such as a Fab fragment, and its Ag, the term paratope is herein, unless otherwise specified or contradicted by context, specifically defined as Ag residues characterised by having a heavy atom (i.e. a non-hydrogen atom) within a distance of 4 Å from a heavy atom in TFPI.

The epitope and paratope for a given antibody (Ab)/antigen (Ag) pair may be identified by routine methods. For example, the general location of an epitope may be determined by assessing the ability of an antibody to bind to different fragments or variant TFPI polypeptides. The specific amino acids within TFPI that make contact with an antibody (epitope) and the specific amino acids in an antibody that make contact with TFPI (paratope) may also be determined using routine methods. For example, the antibody and target molecule may be combined and the Ab:Ag complex may be crystallised. The crystal structure of the complex may be determined and used to identify specific sites of interaction between the antibody and its target.

Antibodies that bind to the same antigen can be characterised with respect to their ability to bind to their common antigen simultaneously and may be subjected to "competition binding"/"binning". In the present context, the term "binning" refers to a method of grouping antibodies that bind to the same antigen. "Binning" of antibodies may be based on competition binding of two antibodies to their common antigen in assays based on standard techniques such as surface plasmon resonance (SPR), ELISA or flow cytometry.

An antibody's "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e. antibodies belonging to the same "bin" may have identical epitopes, overlapping epitopes or even separate epitopes. The latter is the case if the reference antibody bound to its epitope on the antigen takes up the space required for the second antibody to contact its epitope on the antigen ("steric hindrance"). Non-competing antibodies generally have separate epitopes.

The term "binding affinity" is herein used as a measure of the strength of a non-covalent interaction between two molecules, e.g. an antibody, or fragment thereof, and an antigen. The term "binding affinity" is herein used to describe both monovalent and bivalent interactions (intrinsic activity).

Binding affinity between two molecules, e.g. an antibody, or fragment thereof, and an antigen, through a monovalent interaction may be quantified by determining the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{on}$), respectively. $K_D$ is related to $k_a$ and $k_d$ through the equation $K_D=k_d/k_a$.

Following the above definition, binding affinities associated with different molecular interactions, such as comparison of the binding affinity of different antibodies for a given antigen, may be compared by comparison of the $K_D$ values for the individual antibody/antigen complexes.

An antibody according to the current invention may be able to compete with another molecule, such as a naturally occurring ligand or receptor or another antibody, for binding to TFPI and thereby affect functions associated with these interactions. The ability of an antibody to compete with a natural ligand/receptor may be assessed by various activity assays measuring the effect on the apparent $K_i$ for TFPI inhibition. $K_D$ values may then be deduced from apparent $K_i$ values. Typically, the $K_D$ value of interest for the antibody with respect to the target (TFPI) will be 2-fold, preferably 5-fold, more preferably 10-fold lower than the $K_D$ of other TFPI ligands. More preferably, the $K_D$ will be 50-fold less, such as 100-fold less, or 200-fold less; even more preferably 500-fold less, such as 1,000-fold less, or 10,000-fold less.

The value of this dissociation constant can be determined directly by well-known methods. Standard assays to evaluate the binding ability of ligands such as antibodies towards targets are known in the art and include, for example, ELISAs, Western blots, RIAs, isothermal titration calorimetry, and flow cytometry analysis. The binding kinetics and binding affinity of the antibody also can be assessed by standard assays known in the art, such as SPR.

A competitive binding assay can be conducted in which the binding of the antibody to the target is compared to the binding of the target by another ligand of that target, such as another antibody.

A bispecific antibody as disclosed herein may bind full length TFPI or TFPI (1-161) with a greater affinity and/or avidity than the combined affinity of its respective "arms".

A bispecific antibody as disclosed herein may bind full length TFPI with a greater affinity and/or avidity than it binds TFPI (1-96), TFPI (1-76), TFPI (26-76), TFPI (77-161), TFPI (97-147), and/or any other TFPI fragment, as disclosed herein.

A bispecific antibody as disclosed herein may have a $K_D$ for full length TFPI or TFPI (1-161) of $1\times10^{-11}$ M or less, or $1\times10^{-12}$ M or less, or $1\times10^{-13}$ M or less, or $1\times10^{-14}$ M or less, or $1\times10^{-15}$ M or less.

Any "arm" of a bispecific antibody of the invention, may have a $K_D$ for its target of $1\times10^{-5}$ M or less, $1\times10^{-6}$ M or less, $1\times10^{-7}$ M or less, $1\times10^{-8}$ M or less, or $1\times10^{-9}$ M or less, or $1\times10^{-10}$ M or less, $1\times10^{-11}$ M or less, or $1\times10^{-12}$ M or less, or $1\times10^{-13}$ M or less, or $1\times10^{-14}$ M or less, or $1\times10^{-15}$ M or less. The $K_D$ of an antibody of the current invention may be less than 0.8 nM, such as less than 0.7 nM, such as less than 0.6 nM, such as less than 0.5 nM, such as less than 0.4 nM, such as less than 0.3 nM, such as less than 0.2 nM, such as less than 0.1 nM, such as less than 0.05 nM, such as less than 0.025 nM, such as less than 0.015 nM, such as between 0.015 nM and 0 nM.

In one aspect a bispecific conjugate of two (full length) antibodies or Fab fragments as disclosed herein comprises a TFPI (1-79) binder and a TFPI KPI-2 binder, wherein the $K_D$ of the TFPI (1-79) binder is $2\times10^{-9}$ M or less, $3\times10^{-9}$ M or less, $4\times10^{-9}$ M or less, $5\times10^{-9}$ M or less, $6\times10^{-9}$ M or less, $7\times10^{-9}$ M or less, $8\times10^{-9}$ M or less, $9\times10^{-9}$ M or less, $1\times10^{-8}$ M or less, $2\times10^{-8}$ M or less, $3\times10^{-8}$ M or less, $4\times10^{-8}$ M or less, $5\times10^{-8}$ M or less, $6\times10^{-8}$ M or less, $7\times10^{-8}$ M or less, $8\times10^{-8}$ M or less, $9\times10^{-8}$ M or less, $1\times10^{-7}$ M or less, $2\times10^{-7}$ M or less, $3\times10^{-7}$ M or less, $4\times10^{-4}$ M or less, $5\times10^{-7}$ M or less, $6\times10^{-7}$ M or less, $7\times10^{-7}$ M or less, $8\times10^{-7}$ M or less, $9\times10^{-7}$ M or less, $1\times10^{-6}$ M or less, $2\times10^{-6}$ M or less, $3\times10^{-6}$ M or less, $4\times10^{-6}$ M or less, $5\times10^{-6}$ M or less, $6\times10^{-6}$ M or less, $7\times10^{-6}$ M or less, $8\times10^{-6}$ M or less, $9\times10^{-6}$ M or less, $1\times10^{-5}$ M or less, $2\times10^{-5}$ M or less, $3\times10^{-5}$ M or less, $4\times10^{-5}$ M or less, $5\times10^{-5}$ M or less, $6\times10^{-5}$ M or less, $7\times10^{-5}$ M or less, $8\times10^{-5}$ M or less, $9\times10^{-5}$ M or less.

In one aspect the $K_D$ of the TFPI (1-79) binder is in the range $5\times10^{-7}$ M to $1\times10^{-5}$ M.

In one such aspect the $K_D$ of the TFPI (1-79) binder is in the range $1\times10^{-7}$ M to $1\times10^{-5}$ M. In one such aspect the $K_D$ of the TFPI (1-79) binder is in the range $1\times10^{-7}$ M to $1\times10^{-6}$ M.

In one aspect the $K_D$ of the TFPI (1-79) binder is in the range $5\times10^{-7}$ M to $1\times10^{-7}$ M.

In one aspect the $K_D$ of the TFPI (1-79) binder is in the range $1\times10^{-7}$ M to $5\times10^{-5}$ M.

In one aspect the TFPI (1-79) binder is a variant of mAb2F22, Fab 0295 or Fab 0296 comprising one or more substitutions.

In one aspect the KPI-2 binder is a variant of mAb 2021, mAb 0310, Fab 0088 or Fab 0313 comprising one or more substitutions.

In one aspect a bispecific conjugate of two (full length) antibodies or Fab fragments as disclosed herein comprises a TFPI (1-79) binder and a TFPI KPI-2 binder, wherein $K_D$ of the KPI-2 binder is $2\times10^{-9}$ M or less, $3\times10^{-9}$ M or less, $4\times10^{-9}$ M or less, $5\times10^{-9}$ M or less, $6\times10^{-9}$ M or less, $7\times10^{-9}$ M or less, $8\times10^{-9}$ M or less, $9\times10^{-9}$ M or less, $1\times10^{-8}$ M or less, $2\times10^{-8}$ M or less, $3\times10^{-8}$ M or less, $4\times10^{-8}$ M or less, $5\times10^{-8}$ M or less, $6\times10^{-8}$ M or less, $7\times10^{-8}$ M or less, $8\times10^{-8}$ M or less, $9\times10^{-8}$ M or less, $1\times10^{-7}$ M or less, $2\times10^{-7}$ M or less, $3\times10^{-7}$ M or less, $4\times10^{-7}$ M or less, $5\times10^{-7}$ M or less, $6\times10^{-7}$ M or less, $7\times10^{-7}$ M or less, $8\times10^{-7}$ M or less, $9\times10^{-7}$ M or less, $1\times10^{-6}$ M or less, $2\times10^{-6}$ M or less, $3\times10^{-6}$ M or less, $4\times10^{-6}$ M or less, $5\times10^{-6}$ M or less, $6\times10^{-6}$ M or less, $7\times10^{-6}$ M or less, $8\times10^{-6}$ M or less, $9\times10^{-6}$ M or less, $1\times10^{-5}$ M or less, $2\times10^{-5}$ M or less, $3\times10^{-5}$ M or less, $4\times10^{-5}$ M or less, $5\times10^{-5}$ M or less, $6\times10^{-5}$ M or less, $7\times10^{-5}$ M or less, $6\times10^{-5}$ M or less, $5\times10^{-5}$ M or less, $4\times10^{-5}$ M or less, $3\times10^{-5}$ M or less, $2\times10^{-5}$ M or less, $1\times10^{-5}$ M or less.

In one aspect the $K_D$ of the KPI-2 binder is in the range $5\times10^{-7}$ M to $1\times10^{-5}$ M. In one such aspect the $K_D$ of the KPI-2 binder is in the range $1\times10^{-7}$ M to $1\times10^{-5}$ M. In one such aspect the $K_D$ of the KPI-2 binder is in the range $1\times10^{-4}$ M to $1\times10^{-6}$ M.

In one aspect the $K_D$ of the KPI-2 binder is in the range $5\times10^{-7}$ M to $1\times10^{-7}$ M.

In one aspect the $K_0$ of the KPI-2 binder is in the range $1\times10^{-4}$ M to $5\times10^{-5}$ M.

In one aspect a bispecific antibody as disclosed herein comprises a TFPI (1-79) binder having a $K_D$ in the range $1\times10^{-9}$ M to $1\times10^{-6}$ M and a KPI-2 binder having a $K_D$ in the range $1\times10^{-14}$ M to $1\times10^{-10}$ M. In one such aspect the TFPI (1-79) binder $K_D$ is in the range $1\times10^{-8}$ M to $1\times10^{-6}$ M and the KPI-2 binder $K_D$ is in the range $1\times10^{-14}$ M to $1\times10^{-1}$ M.

In one aspect a bispecific antibody as disclosed herein comprises a TFPI (1-79) binder having a $K_D$ in the range $1\times10^{-14}$ M to $1\times10^{-10}$ M and a KPI-2 binder having a $K_D$ in the range $1\times10^{-12}$ M to $1\times10^{-11}$ M.

In one aspect a bispecific antibody as disclosed herein comprises a TFPI (1-79) binder having a $K_D$ in the range $1\times10^{-12}$ M to $1\times10^{-10}$ M and a KPI-2 binder having a $K_D$ in the range $1\times10^{-12}$ M to $1\times10^{-8}$ M. In one such aspect the $K_D$ of the TFPI (1-79) binder is in the range $1\times10^{-11}$ M to $5\times10^{-10}$M and the $K_D$ of the KPI-2 binder is in the range $1\times10^{-10}$ M to $1\times10^{-8}$ M.

In one aspect the TFPI (1-79) binder is mAb 0336 and the KPI-2 binder is mAb 0310.

In one aspect the KPI-2 binder is Fab 0088. In an alternative aspect the KPI-2 binder is Fab 0094. In another alternative aspect the KPI-2 binder is Fab 0313.

In one aspect Fab 0094, Fab 0313, Fab 0094 or Fab 0088 is combined with a KPI-1 binder which is a variant of Fab 0295 comprising one or more substitutions.

In one aspect a synergistic effect on thrombin generation is obtained by combining two antibody fragments binding to TFPI (1-79) and TFPI KPI-2, respectively, into a bispecific antibody.

In one aspect a synergistic effect on thrombin generation is obtained by combining two Fab fragments binding to TFPI (1-79) and TFPI KPI-2, respectively, into a bispecific Fab (BiFab).

In one aspect the synergic effect referred to above may be present even where the affinity of one of arms of a bispecific antibody or Fab against its target is reduced.

In one aspect, the bispecific antibodies of the current invention may compete with FXa, TF/FVIIa and/or TF/FVIIa/FXa for binding to TFPI.

In another aspect, the present invention provides compositions and formulations comprising molecules of the invention, such as the bispecific antibodies described herein.

For example, the invention provides a pharmaceutical composition that comprises one or more bispecific TFPI antibodies of the invention, formulated together with a pharmaceutically acceptable carrier.

Accordingly, one object of the invention is to provide a pharmaceutical formulation comprising such a bispecific TFPI antibody which is present in a concentration from 0.25 mg/ml to 250 mg/ml, and wherein said formulation has a pH from 2.0 to 10.0. The formulation may further comprise one or more of a buffer system, a preservative, a tonicity agent, a chelating agent, a stabiliser, or a surfactant, as well as various combinations thereof. The use of preservatives, isotonic agents, chelating agents, stabilisers and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

A bispecific antibody or a pharmaceutical formulation comprising it may be used to treat a subject with a coagulopathy.

The term "subject", as used herein, includes any human patient, or non-human vertebrate.

The term "coagulopathy", as used herein, refers to an increased haemorrhagic tendency which may be caused by any qualitative or quantitative deficiency of any pro-coagulative component of the normal coagulation cascade, or any upregulation of fibrinolysis. Such coagulopathies may be congenital and/or acquired and/or iatrogenic and are identified by a person skilled in the art.

Non-limiting examples of congenital hypocoagulopathies are haemophilia A, haemophilia B, Factor VII deficiency, Factor X deficiency, Factor XI deficiency, von Willebrand's disease and thrombocytopenias such as Glanzmann's thombasthenia and Bernard-Soulier syndrome. Said haemophilia A or B may be severe, moderate or mild. The clinical severity of haemophilia is determined by the concentration of functional units of FIX/FVIII in the blood and is classified as mild, moderate, or severe. Severe haemophilia is defined by a clotting factor level of <0.01 U/ml corresponding to <1% of the normal level, while moderate and mild patients have levels from 1-5% and >5%, respectively. Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exacerbate this situation. Said haemorrhage may be from any part of the body.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with thrombocytopenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

An antibody of the invention may be administered parenterally, such as intravenously, such as intramuscularly, such as subcutaneously. Subcutaneous administration is preferable.

Alternatively, an antibody of the invention may be administered via a non-parenteral route, such as perorally or topically. An antibody of the invention may be administered prophylactically. An antibody of the invention may be administered therapeutically (on demand).

In one embodiment the bispecific antibodies of the present invention are used to measure TFPIα levels in vitro.

The following are non-limiting embodiments of the invention:

Embodiment 1: A bispecific antibody or BiFab capable of specifically binding a first epitope and a second epitope within positions 1 to 161 of human TFPI (SEQ ID NO: 1).

Embodiment 2: The bispecific antibody according to embodiment 1, wherein said first epitope is within positions 1-76 and said second epitope is within positions 77-161 of human TFPI.

Embodiment 3: The bispecific antibody according to embodiment 1, wherein said first epitope is within positions 1-96 and said second epitope is within positions 97-161 of human TFPI.

Embodiment 4: The bispecific antibody according to any one of embodiments 2-3, wherein said first epitope is within the Kunitz-type inhibitor 1 domain (residues 26-76) of human TFPI.

Embodiment 5: The bispecific antibody according to any one of embodiments 2-3, wherein said second epitope is within the Kunitz-type inhibitor 2 domain (residues 97-147) of human TFPI.

Embodiment 6: The bispecific antibody according to embodiment 5, wherein said KPI-1 epitope comprises amino acid residues Arg 41, Arg 65 and/or Glu 67 of SEQ ID NO: 1.

Embodiment 7: The bispecific antibody according to any one of embodiments 4 or 6, wherein said KPI-1 epitope comprises amino acid residues Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gin 63, Arg 65, Phe 66, Glu 67, Glu 71 and Met 75 of SEQ ID NO: 1.

Embodiment 8: The bispecific antibody according to embodiment 5 wherein said second epitope comprises amino acid residue Arg 107 of SEQ ID NO: 1.

Embodiment 9: The bispecific antibody according to embodiment 5, wherein said second epitope comprises amino acid residues Glu 100, Glu 101, Asp 102, Pro 103, Arg 107, Tyr 109, Thr 111, Tyr 113, Phe 114, Asn 116, Gin 118, Gin 121, Cys 122, Glu 123, Arg 124, Phe 125, Lys 126 and Leu 140 of SEQ ID NO: 1.

Embodiment 10: The bispecific antibody according to embodiment 1, wherein the heavy chain of a first antigen recognition site comprises:
- a CDR1 sequence corresponding to amino acids 31 to 35 of SEQ ID NO: 4 (SYGVH), SEQ ID NO: 6 (NYGVH) or SEQ ID NO: 8 (GYGVH), wherein one of these amino acid residues may be substituted by a different amino acid residue; and/or
- a CDR2 sequence corresponding to amino acids 50 to 65 of SEQ ID NO: 4 (VIWRGGSTDFNAAFMS), SEQ ID NO: 6 (VIWRGGSIDYNAAFMS) or SEQ ID NO: 8 (VIWRGGSIDYNAAFMS), wherein one, two or three of these amino acids may be substituted by a different amino acid residue; and/or
- a CDR3 sequence corresponding to amino acids 98 to 110 of SEQ ID NO: 4 (NSHGNYVGYAMDY), SEQ ID NO: 6 or SEQ ID NO: 8 (NSHGNYVGYAMDY), wherein one or two of these amino acid residues may be substituted by a different amino acid;

and wherein the light chain of said first antigen recognition site comprises:
- a CDR1 sequence corresponding to amino acids 24 to 34 (KASENVGAAVA) of SEQ ID NO: 5, SEQ ID NO: 7 (KASQSVGPAVA) or SEQ ID NO: 9 (KASQNVGTAVA), wherein one, two or three of these amino acid residues may be substituted by a different amino acid residue; and/or
- a CDR2 sequence corresponding to amino acids 50 to 56 (SASNRYT) of SEQ ID NO: 5, SEQ ID NO: 7 or SEQ ID NO: 9 (SASNRYT), wherein one of these amino acid residues may be substituted by a different amino acid residue; and/or
- a CDR3 sequence corresponding to amino acids 89 to 96 (QQYTNYPT) of SEQ ID NO: 5, SEQ ID NO: 7 (QQYTSYPT) or SEQ ID NO: 9 (QQYTSYPT), wherein one of these amino acid residues may be substituted by a different amino acid residue.

Embodiment 11: The bispecific antibody according to embodiment 1, wherein the heavy chain of a first antigen recognition site comprises:
- a CDR1 sequence corresponding to amino acids 31 to 35 of SEQ ID NO: 4 (SYGVH), SEQ ID NO: 6 (NYGVH) or SEQ ID NO: 8 (GYGVH); and
- a CDR2 sequence corresponding to amino acids 50 to 65 of SEQ ID NO: 4 (VIWRGGSTDFNAAFMS), SEQ ID NO: 6 (VIWRGGSIDYNAAFMS) or SEQ ID NO: 8 (VIWRGGSIDYNAAFMS); and
- a CDR3 sequence corresponding to amino acids 98 to 110 of SEQ ID NO: 4, SEQ ID NO: 6 or SEQ ID NO: 8 (NSHGNYVGYAMDY);

and wherein the light chain of said first antigen recognition site comprises:
- a CDR1 sequence corresponding to amino acids 24 to 34 of SEQ ID NO: 5 (KASENVGAAVA), SEQ ID NO: 7 (KASQSVGPAVA) or SEQ ID NO: 9 (KASQNVGTAVA); and
- a CDR2 sequence corresponding to amino acids 50 to 56 of SEQ ID NO: 5, SEQ ID NO: 7 or SEQ ID NO: 9 (SASNRYT); and
- a CDR3 sequence corresponding to amino acids 89 to 96 of SEQ ID NO: 5 (QQYTNYPT), SEQ ID NO: 7 (QQYTSYPT) or SEQ ID NO: 9 (QQYTSYPT).

Embodiment 12: The bispecific antibody according to embodiment 1, wherein the heavy chain of a first antigen recognition site comprises:
- a CDR1 sequence corresponding to amino acids 31 to 35 of SEQ ID NO: 6 (NYGVH); and
- a CDR2 sequence corresponding to amino acids 50 to 65 of SEQ ID NO: 6 (VIWRGGSIDYNAAFMS); and
- a CDR3 sequence corresponding to amino acids 98 to 110 of SEQ ID NO: 6 (NSHGNYVGYAMDY);

and wherein the light chain of said first antigen recognition site comprises:
- a CDR1 sequence corresponding to amino acids 24 to 34 of SEQ ID NO: 7 (KASQSVGPAVA); and
- a CDR2 sequence corresponding to amino acids 50 to 56 of SEQ ID NO: 7 (SASNRYT); and
- a CDR3 sequence corresponding to amino acids 89 to 96 of SEQ ID NO: 7 (QQYTSYPT).

Embodiment 13: The bispecific antibody according to embodiment 1, wherein the heavy chain of a first antigen recognition site comprises:
- a CDR1 sequence corresponding to amino acids 31 to 36 of SEQ ID NO: 10 (SDYAWN), wherein one of these amino acid residues may be substituted by a different amino acid residue; and/or
- a CDR2 sequence corresponding to amino acids 51 to 66 of SEQ ID NO: 10 (YISYSGSTSYNPSLKS), wherein one, two or three of these amino acids may be substituted by a different amino acid residue; and/or
- a CDR3 sequence corresponding to amino acids 99 to 104 of SEQ ID NO: 10 (WAYDGP), wherein one of these amino acid residues may be substituted by a different amino acid, and wherein the light chain of said first antigen recognition site comprises:
- a CDR1 sequence corresponding to amino acids 24 to 33 (RASSSVSHMH) of SEQ ID NO: 11, wherein one or two of these amino acid residues may be substituted by a different amino acid residue; and/or a CDR2 sequence corresponding to amino acids 49 to 55 (ATSNLAS) of SEQ ID NO: 11, wherein one of these amino acid residues may be substituted by a different amino acid residue; and/or a CDR3 sequence corresponding to amino acids 88 to 96 (QQWSSNPFT) of SEQ ID NO: 11, wherein one of these amino acid residues may be substituted by a different amino acid residue.

Embodiment 14: A bispecific antibody according to any one of embodiments 10-13, wherein the heavy chain of a second antigen recognition site comprises:

a CDR1 sequence corresponding to amino acids 31 to 35 (NYAMS) of SEQ ID NO:19, wherein one of these amino acids may be substituted by a different amino acid; and/or a CDR2 sequence corresponding to amino acids 50 to 66 of SEQ ID NO:19 (TISRSGSYSYFPDSVQG), SEQ ID NO: 21 TISRSGSYSYYPDSVKG or SEQ ID NO: 25 (TISRSGSYSYYADSVKG), wherein one, two or three of these amino acids may be substituted by a different amino acid; and/or a CDR3 sequence corresponding to amino acids 99 to 110 (LGGYDEGDAMDS) of SEQ ID NO:19, wherein one, two or three of these amino acids may be substituted by a different amino acid.

and wherein the light chain of said second antigen recognition site comprises:

a CDR1 sequence corresponding to amino acids 24 to 39 (KSSQSLLESDGKTYLN) of SEQ ID NO: 20, wherein one, two or three of these amino acids may be substituted with a different amino acid; and/or a CDR2 sequence corresponding to amino acids 55 to 61 (LVSILDS) of SEQ ID NO: 20, wherein one or two of these amino acids may be substituted with a different amino acid; and/or a CDR3 sequence corresponding to amino acids 94 to 102 (LQATHFPQT) of SEQ ID NO: 20, wherein one or two of these amino acids may be substituted with a different amino acid.

Embodiment 15: The bispecific antibody according to any one of embodiments 10-14, wherein said substitution is a conservative substitution.

Embodiment 16: The bispecific antibody according to any one of the preceding embodiments, selected from the group consisting of a full length bispecific antibody and a chemical conjugate of two antigen binding fragments.

Embodiment 17: The bispecific antibody according to embodiment 16, which is a conjugate of two Fab fragments.

Embodiment 18: The bispecific antibody according to any one of embodiments 1-17, which is humanised or human.

Embodiment 19: The bispecific antibody according to any one of embodiments 1-18, which has a binding affinity for full length TFPI or TFPI (1-161) of $1 \times 10^{-11}$ M or less, or $1 \times 10^{-12}$ M or less, or $1 \times 10^{-13}$ M or less, or $1 \times 10^{-14}$ M or less, or $1 \times 10^{-15}$ M or less.

Embodiment 20: A pharmaceutical composition comprising the bispecific antibody according to any one of embodiments 1 to 18 and a pharmaceutically acceptable carrier.

Embodiment 21: The bispecific antibody according to any one of embodiments 1 to 19 or the pharmaceutical composition according to embodiment 20 for use as a medicament.

Embodiment 22: The bispecific antibody according to any one of embodiments 1 to 19 or the pharmaceutical composition according to embodiment 20 for use in the treatment of coagulopathy.

Embodiment 23: The bispecific antibody for use according to embodiment 22, wherein said subject has a congenital, acquired and/or iatrogenic coagulopathy, such as haemophilia A, with or without inhibitors, or haemophilia B, with or without inhibitors.

Embodiment 24: A method of treating a subject with a coagulopathy, comprising administering to said subject the bispecific antibody according to any one of embodiments 1 to 19.

Embodiment 25: Use of the bispecific antibody according to any one of embodiments 1-19 for the manufacture of a medicament for the treatment of a coagulopathy.

Embodiment 26: Use according to embodiment 25, wherein said coagulopathy is a congenital, acquired and/or iatrogenic coagulopathy.

Embodiment 27: Use according to embodiment 26, wherein said coagulopathy is haemophilia A, with or without inhibitors, or haemophilia B, with or without inhibitors.

The present invention is further illustrated by the following examples which should not be construed as further limiting. The contents of all figures and all references, patents and published patent applications cited throughout this application are expressly incorporated herein by reference.

EXAMPLES

Example 1: Immunisation, Fusion and Screening

RBF mice were immunised with human TFPIα (SEQ ID NO: 1) or TFPI (1-161) (SEQ ID NO: 2). Mice were injected subcutaneously: 20 μg human TFPI was mixed with complete Freund's adjuvant for the first injection. For subsequent immunisations, incomplete Freund's adjuvant was used with the same concentration of the antigen. Ten days after the final immunisation, eye-blood from mice was screened, using ELISA, for human TFPI specific antibodies. Mice with positive serum titres were boosted with 10 μg of human TFPIα or TFPI (1-161) by intravenous injection and sacrificed after three days. The spleens were removed aseptically and dispersed to a single cell suspension. Fusion of spleen cells and myeloma cells was done by means of the PEG-method or by electrofusion. The resulting hybridoma cells were cloned by limiting dilution into microtiter plates. Supernatants from individual hybridomas were initially screened by ELISA for expression of antibodies capable of binding to full-length TFPIα or TFPI (1-161). To identify hybridomas producing antibodies specific for TFPI (1-79), the hybridomas positive for binding to full-length TFPIα or TFPI (1-161) were counter screened for binding to the TFPI KPI-2 fragment (represented by amino acid residues 97-147 of SEQ ID NO: 1). Hybridomas positive for binding to TFPI (1-161) and negative for binding to the TFPI KPI-2 fragment were isolated and expanded for production of antibody.

Antibodies were purified from supernatants by standard protein A affinity chromatography and used to determine binding and affinity to human TFPIα and TFPI (1-79) and TFPI neutralising activity in plasma (TGT assay). Hybridomas producing antibodies of interest, i.e., those specific for TFPI (1-79) were subcloned by limited dilution and the original antibody profile was verified for material from subcloned hybridomas. Cells from subcloned hybridomas were used for isolation of RNA and subsequent antibody cloning and sequence identification.

Example 2: Cloning and Sequencing of Mouse Anti-Human TFPI (1-79) Specific Antibodies This example describes cloning and sequencing of the murine heavy chain and light chain sequences of TFPI antibodies mAb 2F3, mAb 2F22, mAb 2F45, mAb 1F56, and mAb 1F91. Total RNA was extracted from hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. The reverse primer with the sequence shown in SEQ ID NO: 12 was used for HC (VH domain) amplification and the reverse primer with the sequence shown in SEQ ID NO: 13 was used for LC amplification. PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 E. coli(Life Technologies). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at MWG Biotech, Martinsried Germany using M13uni(-21)/M13rev(-29) sequencing primers. Sequences were analysed and annotated using the Vector NTI Advance 11 program (Life Technologies). All kits and reagents were used according to the manufacturer's instructions.

A single unique murine kappa type LC and a single unique murine HC, subclass IgG1 was identified for each of the hybridomas: mAb 2F3, mAb 2F22, mAb 2F45 and mAb 1F91. The LC and HC sequences of mAb 1F56 showed that this antibody is identical in sequence to mAb 1F91. Amino acid sequences for the variable heavy chain and variable light chain sequences (excluding leader peptide sequences) are shown in SEQ ID NOs 4-11.

Generation of Antibody LC and HC Expression Vectors

CMV promoter-based expression vectors (pTT vectors) were generated for transient expression of mouse-human chimeric versions of mAb 2F22. The pTT vectors are developed for transient protein expression by Yves Durocher (Durocher et al. Nucleic Acid Research, 2002). In addition to the CMV promotor, the pTT-based vectors contain a pMB1 origin, an EBV origin and the Amp resistance gene.

An expression vector was generated of a chimeric mAb 2F22 light chain, carrying the murine 2F22 light chain variable region and a human kappa constant region for mAb 0294, Fab 0296 and Fab 0295 expression (SEQ ID NO: 15). Expression vectors were generated for a chimeric mAb 2F22 heavy chain carrying the murine 2F22 heavy chain variable region and a full length human IgG4 (S241P) constant region for mAb 0294 expression (SEQ ID NO: 17) or truncated human IgG4 constant regions for Fab 0296 expression (SEQ ID NO: 14) or Fab 0295 expression (SEQ ID NO: 18).

A pTT-based LC expression vector was generated for transient expression of chimeric mAb 2F22 antibody and antibody fragment. Initially, the region corresponding to the VL domains of mAb 2F22 was PCR amplified in a 2-step reaction from an original TOPO sequencing clone, using primers specific for the N and C-terminal sequences. The original murine signal peptide was exchanged for the human CD33 signal peptide by 2-step overlapping PCR. The primary sense primers carries the C-terminal part of the CD33 signal peptide sequence and the secondary sense primer contained a HindIII restriction site for cloning purposes, a Kozak sequence (5'-GCCGCCACC-3') immediately upstream of the ATG start codon and the N-terminal part of the CD33 signal peptide sequences. The anti-sense primer contained an in-frame BsiWI restriction site in the VL/CL transition sequence. The amplified fragment was cloned into a linearized pTT-based vector containing the sequence for a human kappa CL domain and subsequently transformed into E. coli for selection. The sequence of the final construct was verified by DNA sequencing.

pTT-based HC expression vectors were generated for transient expression of a chimeric mAb 2F22 and Fab 2F22 fragments. The chimeric mAb and Fab fragments are referred to as mAb 0294, Fab 0296 and Fab 0295, respectively. Initially, the region corresponding to the VH domain of mAb 2F22 was PCR amplified in a 2-step reaction from an original TOPO sequencing clone, using primers specific for the N- and C-terminal sequences. The original murine signal peptide was exchanged for the human CD33 signal peptide by 2-step overlapping PCR. The primary sense primers carries the C-terminal part of the CD33 signal peptide sequence and the secondary sense primer contained a HindIII restriction site for cloning purposes, a Kozak sequence (5'-GCCGCCACC-3') immediately upstream of the ATG start codon and the N-terminal part of the CD33 signal peptide sequences. The anti-sense primer contained an in-frame NheI restriction site at the VH/CH transition. For generation of full length HC expression vector (HC of mAb 0294), the generated VH domain PCR fragment was restriction digested and cloned into a linearized pTT-based vector containing the sequence for a human IgG4 (S241P) constant region. The IgG4 hinge mutation Serine 241 to Proline is included to stabilize the IgG4 antibody by eliminating formation of half-antibodies. The mutated hinge position is referred to as S241P when numbered according to Kabat or alternatively S228P, when numbered according to the EU index.

For generation of the truncated HC expression vector for Fab 0296 expression, the generated VH domain PCR fragment was restriction digested and cloned into a linearized pTT-based vector containing the sequence for a truncated human IgG4 constant region. The IgG4-based HC was truncated in the hinge region after the human IgG4 hinge lysine residue as seen in the sequence of the Fab 0296 HC (SEQ ID NO: 14). The cloning reaction was subsequently transformed into E. coli for selection. The sequence of the final construct was verified by DNA sequencing.

For generation of the truncated HC expression vector for Fab 0295 expression, the generated VH domain PCR fragment was restriction digested and cloned into a linearized pTT-based vector containing the sequence for a second truncated human IgG4 constant region. The IgG4-based HC for Fab 0295 was truncated in the hinge region after the first cysteine residue of the human IgG4 hinge as seen in the sequence of the Fab 0295 HC (SEQ ID NO: 18). The cloning reaction was subsequently transformed into E. coli for selection. The sequence of the final construct was verified by DNA sequencing.

Expression and Purification of mAb and Fab Fragments

The anti-TFPI antibodies and Fab fragments were expressed transiently in suspension cultures of EXP1293F cells (Life Technologies), by co-transfection of the pTT-based LC and HC expression vectors. The following procedure describes the generic transfection protocol used for suspension adapted EXPI293F cells.

EXPI293F Transfection

1) Separate dilutions of DNA and transfection reagent are initially prepared.
    a) Use a total of 1 µg of vector DNA (0.5 ug LC vector and 0.5 ug HC vector) per ml cell culture. Dilute the DNA in Opti-MEM media (Gibco) 50 μl medium/μg DNA, mix and incubate at room temperature (23-25° C.) for 5 min.
b) Use Expifectamin™ 293 (Life Technologies) as transfection reagent at a concentration of 2.7 μl per μg DNA. Dilute the Expifectamin™ solution 18.5× in Opti-MEM media (Gibco), mix and incubate at room temperature (23-25° C.) for 5 min.
2) Mix DNA and Expifectamin™ 293 dilutions and leave to incubate at room temperature (23-25° C.) for 10 min.
3) Add the DNA-Expifectamin™ 293 mix directly to the EXP1293F cell culture.

specifications. Biotin-labelled antibody was captured on streptavidin Fortebio sensortips (PALL Life Sciences) followed by binding of human TFPIα followed by binding of mAb 1F91, mAb 2F3, mAb 2F22, mAb 2F45, Bay 2A8-K95L, MBS532510 or 10R-T141A. Results are shown in Table 1 ("Yes" signifies that mAbs compete for binding to TFPI. "No" signifies that mAbs do not compete for binding to TFPI).

These data show that the antibodies fall into 3 different bins, indicating that they have different binding epitopes. Bin 1: mAb 1F91, MBS532510, and 10R-T141A. Bin 2: mAb 2F3, 2F22 and 2F45. Bin 3: Bay2A8 K95L.

TABLE 1

Competition between the indicated TFPI antibodies for binding to TFPI

| 1st mAB | 2nd mAB | | | | | | |
|---|---|---|---|---|---|---|---|
| | 1F91 | 2F3 | 2F22 | 2F45 | Bay2A8-K95L | MBS532510 | 10R-T141A |
| biotin-1F91 | Yes | Yes | Yes | Yes | Yes | Yes | Yes |
| biotin-2F3 | Yes | Yes | Yes | Yes | No | Yes | Yes |
| biotin-2F22 | Yes | Yes | Yes | Yes | No | Yes | Yes |
| biotin-2F45 | Yes | Yes | Yes | Yes | No | Yes | Yes |
| biotin-Bay2A8-K95L | Yes | No | No | No | Yes | Yes | Yes | a) At the time of transfection the cell density of the EXP1293F culture should be 2.8-3.2×10$^6$ cells/mi.
4) Transfer the transfected cell culture to an orbital shaker incubator at 36.5° C., 8% $CO_2$ and 85-125 rpm.
5) 18 hrs post transfection, add 5 ul Expifectamin™ 293 Transfection Enhancer1/ml culture and 50 ul Expifectamin™ 293 Transfection Enhancer2/ml culture and return culture to an orbital shaker incubator at 36.5° C., 8% $CO_2$ and 85-125 rpm.
6) 5 days post transfection, cell culture supernatants were harvested by centrifugation, followed by filtration through a 0.22 μm PES filter unit (Corning).

General Purification Protocol mAb variants were purified by standard affinity chromatography using MabSelect SuRe resin from GE Healthcare according to manufacturer's instructions. The purified antibodies were buffer exchanged to PBS buffer pH 7.2.

Fab fragments were purified by standard affinity chromatography using KappaSelect resin developed by GE Healthcare. The purified Fab fragments were buffer exchanged to PBS buffer pH 7.2. Quality assessment and concentration determination was done by SEC-HPLC.

Example 3: Antibody Binning

Competition between TFPI antibodies 1F91, 2F3, 2F22, 2F45, MBS532510 (MyBioSource.com), 10R-T141A (Fitzgerald Industries International) and Bay 2A8-K95L for binding to full-length TFPIα was measured using Biolayer Interferometry (Fortebio Octet RED384 instrument, PALL Life Sciences). (Bay 2A8 is a human IgG4 (S241P) antibody variant of the 2A8 Fab, disclosed in WO2010/017196. Bay 2A8-K95L is a human IgG4 (S241P) antibody variant of Bay 2A8 carrying the K95L substitution (Kabat numbering) in HC CDR3 (identical to the substitution found in "Fab B" relative to 2A8 as disclosed in WO2012/135671).) mAb 1F91, mAb 2F3, mAb 2F22, mAb 2F45, and Bay 2A8-K95L were randomly labelled with biotin on lysine residues using a 1:1.2 mol mAb:mol biotin-reagent (Thermo Scientific cat #21335) ratio and otherwise following the manufacturer's Example 4: Crystal Structure of TFPI (1-79) in Complex with a Fab Fragment of mAb 2F22

The 3D structure of the N-terminal part of human TFPI (1-79), which consists of an acidic N-terminal region and Kunitz-type Protease Inhibitor domain 1 (KPI-1) (SEQ ID NO: 16), in complex with a Fab fragment, Fab 0296 (SEQ ID NOs: 14 and 15) of mAb 2F22 was determined to high resolution using X-ray crystallography. The results demonstrate that the antibody is capable of binding the KPI-1 of TFPI, and part of the preceding N-terminal. The resulting human TFPI epitope residues comprise Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75 (SEQ ID NO: 2).

Materials and Methods

For crystallographic purpose CMV promoter-based expression vectors (pTT vectors) were generated for transient expression of the Fab fragment corresponding to mAb 2F22 antibody fragment for crystallography as described in Example 2.

The Fab fragment of mAb 2F22 was expressed in a murine-human chimeric form Fab 0296 (SEQ ID NO: 14 and 15) in EXP1293F cells and purified by standard affinity chromatography using KappaSelect resin as described in Example 2.

Human TFPI KPI-1, including the N-terminal part of human TFPI, and, additionally, a GSSGSSG tag N-terminally attached (SEQ ID NO: 16) and Fab 0296 which consists of a light chain corresponding to SEQ ID NO: 15 and a heavy chain fragment corresponding to SEQ ID NO: 14, both in phosphate buffered saline (PBS) buffer (4 tablets in 2 litres of water, GIBCO Cat. No. 18912-014 Invitrogen Corporation), were mixed with a slight molar excess (1.1:1) of the TFPI species. The complex was then concentrated to about 10.0 mg/ml using an Amicon Ultra-4 centrifugal filter with a 10,000 Da molecular weight cut-off. Crystals were grown by the sitting drop-technique using a 96 wells TTP IQ plate from TTP Lab Tech no: 4150-05800 and 100 μl precipitant solution per well. The precipitant solution contained 20% w/v PEG 3350, 200 mM potassium formate and was mixed with the protein solution in a ratio of 3:1. Initial total drop size was 200 nl and crystals appeared after a few days. A crystal was prepared for cryo-freezing by transferring 1 μl of a cryo-solution mix containing 75% of the precipitant solution and 25% glycerol to the drop containing the crystal. The soaking was allowed for about 2 minutes. The crystal was then fished, flash frozen in liquid $N_2$ and kept at a temperature of 100 K by a cryogenic $N_2$ gas stream during data collection. Crystallographic data were collected, to 1.65 Å resolution at beam-line BL911-3 at MAX-lab, Lund, Sweden. Space group determination, integration and scaling of the data were made by the XDS software package [Kabsch, W., J. Appl. Crystallogr., (1993), Vol. 26, pages 795-800]. The space group was determined to be C2 and the cell parameters for the synchrotron data were determined to be 89.010, 66.660, 106.110 Å, respectively, and with a β angle of 111.18°. The R-sym to 1.65 Å resolution was 8.4% and completeness 99.5%. Mean of intensity/sigma (intensity) of unique reflections were equal to 2.0 at around 1.8 Å resolution.

The molecular replacement (MR) method was used for structure determination using the coordinates of a Fab molecule with accession code 1NGZ [Yin, J. et al, Proc Natl Acad Sci USA. 2003 Feb. 4, (100), Vol. 100 pages 856-861] of the Protein Data Bank (PDB) [Berman, H. M. et al, Nucleic Acids Res., (2000), Vol. 28, pages 235-242]. The Fab molecule was divided into two domains, the variable and the constant domains, which each was used as search model in the MR calculations. The Molrep software [Vagin, A. et al, J. Appl. Crystallogr., (1997), Vol. 30, pages 1022-1025] of the CCP4 package [Collaborative Computational Project, N., Acta crystallographica. Section D, Biological crystallography, (1994), Vol. 50, pages 760-763] was used to find the positions of the constant and variable Fab domains. The KPI-1 domain was not found in the MR step, however, the difference electron density map indicated the approximate positions of the KPI-1 domain molecules at this stage. Electron density improvements by the DM software of the CCP4 software package, followed by automated model building and phase improvements using the ARP-wARP software [Langer, G. et al, Nat Protoc, (2008), Vol. 3, pages 1171-1179][Murshudov, G. N. et al, Acta Crystallographica Section D Biological Crystallography, (2011), Vol. 67, pages 355-367] gave an almost complete structure of both the Fab 0296 molecule and of the KPI-1 domain structure, and part of the N-terminal preceding the KPI-1 domain. For the TFPI (SEQ ID NO: 2) residues from 15 to 77 are included in the X-ray model which in addition to the KPI-1 domain also includes some residues N-terminally of KPI-1 (residues 26-76). For the Fab 0296 fragment the light chain residues 1 to 212 and the heavy chain residues 1 to 221 are observed. A procedure of computer graphics inspection of the electron density maps, model corrections and building using the Coot software program [Emsley, P. et al, Acta Crystallogr.Sect.D-Biol.Crystallogr., (2004), Vol. 60, pages 2126-2132] followed by crystallographic refinements, using the software programs Refmac5 [Murshudov, G. N. et al, Acta Crystallographica Section D Biological Crystallography, (2011), Vol. 67, pages 355-367] of the CCP4 software package was entered. The procedure was cycled until no further significant improvements could be made to the model. Final R- and R-free for all data to 1.65 Å resolution were 0.192 and 0.220, respectively.

Results

Calculation of the average areas excluded in pair-wise interactions by the software program Areaimol (Lee, B. et al, J Mol Biol, (1971), Vol. 55, pages 379-400] [Saff, E. B. et al, Math Intell, (1997), Vol. 19, pages 5-11] of the CCP4 program suite [Collaborative Computational Project, N., Acta crystallographica.Section D, Biological crystallography, (1994), Vol. 50, pages 760-763] gave for the human TFPI fragment/anti-TFPI mAb 2F22 Fab fragment molecular complex of the crystal structure 1195 $Å^2$.

The direct contacts between the TFPI KPI-1, inclusive the N-terminal part of TFPI observed in the crystal structure, (SEQ ID NO: 2) and Fab 0296 (SEQ ID NOs: 14 and 15), were identified by running the Contacts software of the CCP4 program suite [Bailey, S., Acta Crystallogr.Sect.D-Biol.Crystallogr., (1994), Vol. 50, pages 760-763] using a cut-off distance of 4.0 Å between the Fab 0296 and the TFPI fragment molecules. The results from the soluble TFPI fragment/Fab 0296 complex crystal structure are shown in Table 2.

The resulting TFPI KPI-1, including the TFPI N-terminal region, epitope for Fab 0296 was found to comprise the following residues of TFPI (using sequence numbering as of SEQ ID NO: 2): Leu 16, Pro 17, Leu 19, Lys 20, Leu 21, Met 22, Phe 25, Cys 35, Ala 37, Met 39, Arg 41, Tyr 56, Gly 57, Gly 58, Cys 59, Glu 60, Gly 61, Asn 62, Gln 63, Arg 65, Phe 66, Glu 67, Glu 71 and Met 75. Evaluated from distances, charge-charge interactions, hydrogen bonds, polar and hydrophobic interactions and low solvent accessibility the following residues seems to be particularly important residues of the epitope: Arg 41, Arg 65 and Glu 67 (SEQ ID NO. 2).

Thus, the TFPI epitope of mAb 2F22 (represented by Fab 0296) comprises residues preceding the KPI-1 domain, including a short N-terminal α-helix, residues in the loop before β-strands 1 of the KPI-1 domain and residues in the beginning of β-strand 1. It also includes residues in the end of β-strand 2 and residues in the loop between β-strand 2 and the C-terminal α-helix of KPI-1 and residues within the C-terminal α-helix of KPI-1.

Hence, the results show that Fab 0296, and thus mAb 2F22 specifically binds to TFPI KPI-1 and part of the preceding N-terminal region.

The Fab 0296 paratope for TFPI KPI-1, includes residues Val 2, Phe 27, Tyr 32, Trp 52, Arg 53, Gly 54, Gly 55, Ser 56, Ile 57, Asp 58, Tyr 59, Ala 61, Met 64, Lys 97, Ser 99, His 100, Asn 102, Tyr 103, Val 104, Gly 105 and Tyr 106 of the heavy (H) chain (SEQ ID NO: 14, Table 2), and residues Pro 31, Ala 32, Tyr 49, Ser 50, Asn 53, Tyr 55, Thr 56, Tyr 91, Thr 92, Ser 93 and Tyr 94 of the light (L) chain (SEQ ID NO: 15, Table 2).

TABLE 2

Data from TFPI (1-79)/Fab 0296 complex crystal structure
TFPI KPI-1, chain K, (SEQ ID NO: 2) interactions with the heavy chain (chain H) of Fab 0296 (SEQ ID NO: 14) and light chain (chain L) of Fab 0296 (SEQ ID NO: 15) for the crystallographic complex. A distance cut-off of 4.0 Å was used. The contacts were identified by the CONTACT computer software program of the CCP4 suite [Collaborative Computational Project, N., Acta crystallographica. Section D, Biological crystallography, (1994), Vol. 50, pages 760-763].

| Human TFPI | | | Fab 0296 | | | | |
|---|---|---|---|---|---|---|---|
| Res. Type | Res. # and Chain | Atom name | Res. Type | Res. # and Chain | Atom name | Distance [Å] | Possibly H-bond |
| Leu | 16K | CB | Tyr | 32H | OH | 3.77 | |
| Leu | 16K | CD1 | Phe | 27H | CB | 3.99 | |
| | | | Tyr | 32H | CZ | 3.78 | |
| | | | Tyr | 32H | CE2 | 3.86 | |
| | | | Tyr | 32H | OH | 3.40 | |
| | | | Lys | 97H | CE | 3.77 | |
| Leu | 16K | CD2 | Val | 2H | CG2 | 3.74 | |
| Pro | 17K | CG | Thr | 56L | OG1 | 3.68 | |

TABLE 2-continued

Data from TFPI (1-79)/Fab 0296 complex crystal structure
TFPI KPI-1, chain K, (SEQ ID NO: 2) interactions with the heavy chain
(chain H) of Fab 0296 (SEQ ID NO: 14) and light chain (chain L) of
Fab 0296 (SEQ ID NO: 15) for the crystallographic complex. A distance
cut-off of 4.0 Å was used. The contacts were identified by the
CONTACT computer software program of the CCP4 suite [*Collaborative
Computational Project, N., Acta crystallographica. Section D,
Biological crystallography*, (1994), Vol. 50, pages 760-763].

| Human TFPI | | | Fab 0296 | | | |
|---|---|---|---|---|---|---|
| Res. Type | Res. # and Chain | Atom name | Res. Type | Res. # and Chain | Atom name | Distance [Å] | Possibly H-bond |
| Leu | 19K | CA | Tyr | 49L | OH | 3.80 | |
| Leu | 19K | CB | His | 100H | ND1 | 3.95 | |
| | | | His | 100H | CE1 | 3.46 | |
| | | | His | 100H | NE2 | 3.73 | |
| | | | Tyr | 49L | OH | 3.79 | |
| Leu | 19K | CD1 | Ser | 99H | O | 3.47 | |
| | | | His | 100H | CD2 | 3.85 | |
| | | | His | 100H | NE2 | 3.69 | |
| | | | Tyr | 55L | CE1 | 3.86 | |
| Leu | 19K | C | Tyr | 49L | OH | 3.85 | |
| Lys | 20K | N | Tyr | 49L | CZ | 3.89 | |
| | | | Tyr | 49L | OH | 3.01 | *** |
| Lys | 20K | CA | Tyr | 49L | OH | 3.93 | |
| Lys | 20K | CB | Tyr | 49L | OH | 3.70 | |
| Lys | 20K | CG | Tyr | 49L | OH | 3.51 | |
| Lys | 20K | CD | Tyr | 49L | OH | 3.80 | |
| | | | Asn | 53L | CG | 3.73 | |
| | | | Asn | 53L | OD1 | 3.29 | |
| Lys | 20K | CE | Asn | 53L | OD1 | 3.93 | |
| Lys | 20K | C | His | 100H | CE1 | 3.92 | |
| Lys | 20K | O | His | 100H | ND1 | 3.41 | * |
| | | | His | 100H | CE1 | 2.88 | |
| | | | Tyr | 49L | CE2 | 3.58 | |
| Leu | 21K | CA | Tyr | 106H | OH | 3.73 | |
| Leu | 21K | CB | Tyr | 106H | OH | 3.99 | |
| Leu | 21K | CD2 | Tyr | 103H | CE2 | 3.72 | |
| | | | Tyr | 103H | CD2 | 3.52 | |
| | | | His | 100H | ND1 | 3.89 | |
| | | | Tyr | 106H | OH | 3.87 | |
| Leu | 21K | C | Tyr | 106H | OH | 3.71 | |
| Met | 22K | N | Tyr | 106H | CZ | 3.81 | |
| | | | Tyr | 106H | OH | 2.81 | *** |
| | | | Tyr | 106H | CE2 | 3.87 | |
| Met | 22K | CA | Tyr | 106H | OH | 3.68 | |
| Met | 22K | CB | Tyr | 106H | OH | 3.60 | |
| Met | 22K | CG | Ser | 50L | OG | 3.75 | |
| Met | 22K | SD | Pro | 31L | CG | 3.78 | |
| Met | 22K | CE | Pro | 31L | CG | 3.80 | |
| Met | 22K | O | Tyr | 106H | OH | 3.86 | * |
| Phe | 25K | CZ | Gly | 105H | O | 3.58 | |
| | | | Ala | 32L | CB | 3.89 | |
| Phe | 25K | CE2 | Val | 104H | O | 3.96 | |
| | | | Gly | 105H | CA | 3.87 | |
| | | | Gly | 105H | C | 3.87 | |
| | | | Gly | 105H | O | 3.41 | |
| | | | Tyr | 106H | CE1 | 3.90 | |
| | | | Tyr | 106H | CZ | 3.61 | |
| | | | Tyr | 106H | OH | 3.79 | |
| | | | Tyr | 106H | CE2 | 3.86 | |
| Phe | 25K | CD2 | Val | 104H | O | 3.81 | |
| | | | Tyr | 106H | CZ | 3.81 | |
| | | | Tyr | 106H | OH | 3.59 | |
| Cys | 35K | SG | Ala | 61H | CB | 3.72 | |
| Ala | 37K | CB | Met | 64H | CE | 3.75 | |
| Met | 39K | SD | Ile | 57H | O | 3.21 | |
| Met | 39K | CE | Ser | 56H | CA | 3.87 | |
| | | | Ser | 56H | CB | 3.66 | |
| | | | Ile | 57H | N | 3.44 | |
| | | | Ile | 57H | O | 3.31 | |
| Arg | 41K | NE | Ser | 56H | CB | 3.74 | |
| Arg | 41K | CZ | Ser | 56H | CB | 3.85 | |
| | | | Asp | 58H | OD1 | 3.00 | |
| Arg | 41K | NH1 | Asp | 58H | CG | 3.53 | |
| | | | Asp | 58H | OD1 | 2.67 | *** |
| | | | Asp | 58H | OD2 | 3.65 | * |
| Arg | 41K | NH2 | Ser | 56H | CB | 3.50 | |
| | | | Ile | 57H | N | 3.79 | * |
| | | | Ile | 57H | C | 3.58 | |
| | | | Ile | 57H | O | 3.12 | *** |
| | | | Asp | 58H | CG | 3.78 | |
| | | | Asp | 58H | OD1 | 2.58 | *** |
| Tyr | 56K | CE2 | Asp | 58H | OD1 | 3.40 | |
| Gly | 57K | O | Met | 64H | CE | 3.82 | |
| Gly | 58K | O | Asp | 58H | C | 3.65 | |
| | | | Tyr | 59H | N | 2.83 | *** |
| | | | Tyr | 59H | CB | 3.96 | |
| | | | Tyr | 59H | CD1 | 3.80 | |
| | | | Asp | 58H | CA | 3.56 | |
| | | | Tyr | 59H | CA | 3.82 | |
| | | | Tyr | 59H | O | 3.69 | * |
| Cys | 59K | CA | Tyr | 59H | O | 3.61 | |
| Cys | 59K | CA | Tyr | 59H | O | 3.59 | |
| Cys | 59K | CB | Tyr | 59H | O | 3.52 | |
| Cys | 59K | CB | Tyr | 59H | O | 3.30 | |
| Cys | 59K | SG | Met | 64H | SD | 3.34 | |
| | | | Ala | 61H | CA | 3.60 | |
| | | | Tyr | 59H | O | 3.92 | |
| | | | Ala | 61H | N | 3.94 | |
| | | | Ala | 61H | CB | 3.75 | |
| Cys | 59K | SG | Ala | 61H | CB | 3.85 | |
| Glu | 60K | N | Ser | 93L | O | 3.90 | * |
| Glu | 60K | CA | Ser | 93L | O | 3.25 | |
| | | | Ser | 93L | CB | 4.00 | |
| | | | Ser | 93L | C | 3.99 | |
| Glu | 60K | OE2 | Tyr | 94L | CE1 | 3.99 | |
| Glu | 60K | C | Ser | 93L | O | 3.30 | |
| Glu | 60K | O | Ser | 93L | O | 3.25 | *** |
| Gly | 61K | O | Ser | 93L | CA | 3.27 | |
| | | | Ser | 93L | CB | 3.51 | |
| Asn | 62K | CA | Thr | 92L | O | 3.84 | |
| Gln | 63K | CA | Val | 104H | CG1 | 3.96 | |
| Gln | 63K | CG | Tyr | 91L | O | 3.58 | |
| | | | Gly | 105H | CA | 3.77 | |
| Gln | 63K | CD | Tyr | 91L | O | 3.77 | |
| | | | Thr | 92L | CA | 3.83 | |
| Gln | 63K | OE1 | Thr | 92L | O | 3.95 | * |
| | | | Thr | 92L | CA | 3.87 | |
| Gln | 63K | NE2 | Tyr | 91L | O | 3.65 | * |
| | | | Thr | 92L | CA | 3.98 | |
| | | | Thr | 92L | CG2 | 3.73 | |
| | | | Ala | 32L | CB | 3.74 | |
| Arg | 65K | NE | Asp | 58H | OD1 | 3.91 | * |
| | | | Asp | 58H | OD2 | 3.76 | * |
| Arg | 65K | CZ | Asp | 58H | OD2 | 3.81 | |
| Arg | 65K | NH2 | Asp | 58H | CG | 3.65 | |
| | | | Asp | 58H | OD2 | 2.92 | *** |
| | | | Val | 104H | CG1 | 3.71 | |
| | | | Val | 104H | CG2 | 3.60 | |
| Arg | 65K | O | Val | 104H | CG2 | 3.64 | |
| Phe | 66K | CD1 | Tyr | 103H | CE1 | 3.80 | |
| | | | Tyr | 103H | CD1 | 3.77 | |
| Phe | 66K | CE1 | Tyr | 103H | CE1 | 3.74 | |
| | | | Tyr | 103H | CD1 | 3.63 | |
| Glu | 67K | CB | Asn | 102H | ND2 | 3.46 | |
| | | | Ser | 56H | OG | 3.33 | |
| | | | Gly | 54H | N | 3.40 | |
| | | | Gly | 54H | CA | 3.69 | |
| Glu | 67K | CG | Ser | 56H | OG | 3.32 | |
| Glu | 67K | CD | Trp | 52H | CB | 3.78 | |
| | | | Asn | 102H | ND2 | 3.94 | |

TABLE 2-continued

Data from TFPI (1-79)/Fab 0296 complex crystal structure TFPI KPI-1, chain K, (SEQ ID NO: 2) interactions with the heavy chain (chain H) of Fab 0296 (SEQ ID NO: 14) and light chain (chain L) of Fab 0296 (SEQ ID NO: 15) for the crystallographic complex. A distance cut-off of 4.0 Å was used. The contacts were identified by the CONTACT computer software program of the CCP4 suite [*Collaborative Computational Project, N., Acta crystallographica*. Section D, *Biological crystallography*, (1994), Vol. 50, pages 760-763].

| Human TFPI | | | Fab 0296 | | | |
|---|---|---|---|---|---|---|
| Res. Type | Res. # and Chain | Atom name | Res. Type | Res. # and Chain | Atom name | Distance [Å] | Possibly H-bond |
| | | | Ser | 56H | CB | 3.89 | |
| Glu | 67K | OE1 | Gly | 54H | N | 2.79 | *** |
| | | | Gly | 54H | CA | 3.49 | |
| | | | Trp | 52H | CB | 3.57 | |
| | | | Trp | 52H | C | 3.94 | |
| | | | Arg | 53H | N | 3.47 | * |
| | | | Arg | 53H | CG | 3.98 | |
| | | | Arg | 53H | CD | 3.87 | |
| | | | Arg | 53H | C | 3.84 | |
| | | | Asn | 102H | CG | 3.86 | |
| | | | Asn | 102H | OD1 | 3.93 | * |
| | | | Asn | 102H | ND2 | 2.97 | *** |
| Glu | 67K | OE2 | Gly | 54H | C | 3.27 | |
| | | | Gly | 54H | O | 3.77 | * |
| | | | Gly | 55H | N | 3.51 | * |
| | | | Ser | 56H | N | 3.02 | *** |
| | | | Gly | 54H | N | 3.28 | *** |
| | | | Gly | 54H | CA | 3.27 | |
| | | | Ser | 56H | CA | 3.64 | |
| | | | Ser | 56H | OG | 2.52 | *** |
| | | | Trp | 52H | CB | 3.91 | |
| | | | Ser | 56H | CB | 3.10 | |
| Glu | 71K | CD | Asn | 102H | ND2 | 3.46 | |
| | | | Arg | 53H | NH1 | 3.50 | |
| Glu | 71K | OE1 | Asn | 102H | CB | 3.82 | |
| | | | Asn | 102H | CG | 3.79 | |
| | | | Asn | 102H | ND2 | 2.81 | *** |
| Glu | 71K | OE2 | Arg | 53H | NH2 | 3.78 | * |
| | | | Arg | 53H | CD | 3.65 | |
| | | | Arg | 53H | NE | 3.58 | * |
| | | | Asn | 102H | ND2 | 3.43 | * |
| | | | Arg | 53H | CZ | 3.01 | |
| | | | Arg | 53H | NH1 | 2.28 | *** |
| Glu | 71K | O | Tyr | 103H | CE1 | 3.91 | |
| | | | Tyr | 103H | OH | 3.57 | * |
| Met | 75K | N | Tyr | 103H | OH | 3.80 | * |
| Met | 75K | CB | Tyr | 103H | CE1 | 3.82 | |
| | | | Tyr | 103H | CZ | 4.00 | |
| | | | Tyr | 103H | OH | 3.73 | |

In the last column "***" indicates a strong possibility for a hydrogen bond at this contact (distance <3.3 Å) as calculated by CONTACT, "*" indicates a weak possibility (distance >3.3 Å).
Blank indicates that the program considered there to be no possibility of a hydrogen bond. Hydrogen-bonds are specific between a donor and an acceptor, are typically strong, and are easily identifiable.

These results show that anti-TFPI Fab 0296 specifically binds to TFPI KPI-1 and part of the preceding N-terminal.

Example 5: Cloning and Engineering of mAb 2021 and mAb 2021 Variants

This example describes cloning and engineering of anti-TFPI antibody: mAb 2021 and variants thereof.

Total RNA was extracted from M-hTFPI 4F36A1B2 hybridoma cells using the RNeasy-Mini Kit from Qiagen and used as template for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Start polymerase (Finnzymes) and the universal primer mix (UPM) included in the SMART™ RACE kit as forward primer. A reverse primer with the following sequence was used for HC (VH domain) amplification:

(SEQ ID NO: 12)
5'-CCCTTGACCAGGCATCCCAG-3'

A reverse primer with the following sequence was used for LC amplification:

(SEQ ID NO: 13)
5'-GCTCTAGACTAACACTCATTCCTGTTGAAGCTCTTG-3'

PCR products were separated by gel electrophoresis, extracted using the GFX PCR DNA & Gel Band Purification Kit from GE Healthcare Bio-Sciences and cloned for sequencing using a Zero Blunt TOPO PCR Cloning Kit and chemically competent TOP10 *E. coli* (Invitrogen). Colony PCR was performed on selected colonies using an AmpliTaq Gold Master Mix from Applied Biosystems and M13uni/M13rev primers. Colony PCR clean-up was performed using the ExoSAP-IT enzyme mix (USB). Sequencing was performed at Eurofins MWG Operon, Germany using either M13uni(-21)/M13rev(-29) or T3/T7 sequencing primers. Sequences were analyzed and annotated using the VectorNTI program. All kits and reagents were used according to the manufacturer's instructions.

A single unique murine kappa type LC and a single unique murine HC, subclass IgG1 was identified.

Generation of Expression Vectors for the Grafted Anti-HzTFP/4F36A1B2

A series of CMV promotor-based based expression vectors (pTT vectors) were generated for transient expression of anti-TFPI antibody/antibody fragment in the HEK293-6E EBNA-based expression system developed by Yves Durocher (Durocher et al. Nucleic Acid Research, 2002). In addition to the CMV promotor, the pTT-based vectors contain a pMB1 origin, an EBV origin and the Amp resistance gene.

Based on the cloned murine anti-TFPI4F36A1B2 VH and VL sequences a humanized version of anti-TFPI4F36 was designed by CDR grafting on human germline sequences. DNA sequences for grafted HzTFPI4F36 VH and VL regions were synthesized (GENEART AG) according to the humanization design of the antibody described above. The sequences were obtained with the basic minimal CDR grafting and no additional back mutations. The respective LC and HC germline leader peptide sequences were include in the constructs as well as a Kozak sequence (5'-GCCGC-CACC-3') immediately upstream of the ATG start codon.

pTT-based expression vectors were generated for transient expression of the grafted HzTFPI4F36, antibody as a human kappa/IgG4(S241P) isotype. The proline mutation at position 241 (numbering according to Kabat, corresponding to residue 228 per the EU numbering system (Edelman G. M. et AL., Proc. Natl. Acad. USA 63, 78-85 (1969)) was introduced in the IgG4 hinge region to eliminated formation of monomeric antibody fragments, i.e. "half-antibodies" comprised of one LC and one HC.

For the HC expression vector, the VH fragment was excised by restriction enzyme digest from the GENEART cloning vector and cloned into a linearized pTT-based vector containing the sequence for a human IgG4(S241P) CH domain and subsequently transformed into *E. coli* for selection. The sequence of the final construct was verified by DNA sequencing. For the LC expression vector, the VL fragment was excised by restriction enzyme digest from the GENEART cloning vector and cloned into a linearized pTT-based vector containing the sequence for a human kappa CL domain and subsequently transformed into *E. coli* for selection. The sequence of the final constructs was verified by DNA sequencing.

Site-Directed Mutagenesis to Isolate mAb 2021

A series of human-to-mouse reverse mutation (referred to as back mutations) were generated in the light chain (LC) and heavy chain (HC) of the grafted HzTFPI4F36.

Site-directed mutagenesis was performed to introduce human-to-mouse reverse mutations (henceforth referred to as back mutations) at the specific residues in the grafted HzTFPI4F36 LC/HC constructs to optimize the grafted constructs. Mutations were introduced by two different methods:

1. QuikChange® Site-Directed or Multi Site-Directed Mutagenesis kits from Stratagene were used to introduce point mutations and combination mutations. The kits were used according to the manufacturer's protocol.
2. Standard 2-step overlapping PCR methods were also used to introduce point mutations and to generate combination mutations.

The LC and HC expression plasmids for grafted HzTFPI4F36 were used as templates for the mutagenesis. The sequences of all final constructs were verified by DNA sequencing.

The final sequences for mAb 2021 HC carries a FR2 region with 4 back mutations rendering the framework sequence identical to original mouse FR2 and 3 CDR2 mutants, i.e. a total of 7 HC back mutations (A40T, G42E, G44R, S49 Å, Y59F, A60P, K64Q) compared to the original grafted sequence (numbering according to Kabat). The LC sequence is the grafted HzTFPI4F36 LC sequence. CDRs and frameworks defined according to Kabat.

The amino acid sequences for the VH and VL regions of the final mAb 2021 are listed as SEQ ID NO: 19 and SEQ ID NO: 20, respectively.

In order to improve the expression yield the original signal peptide sequences (human germline sequence) for both HC and LC, were exchanged for the human CD33 signal peptide (SP). The signal peptide sequences were exchanged by standard PCR amplification of the HC or LC fragment with primers containing a Kozak element (GCCGCCACC), start codon and the CD33 signal sequence (sense primer) and stop codon and EcoRI restriction site (anti-sense primer). The amplified fragments were cloned into linearized pTT-based vectors and transformed into *E. coli* for selection. The sequence of the final construct was verified by DNA sequencing.

Generation of Lower Affinity Variants of mAb 2021

During humanization of anti-TFPI4F36A1B2 to obtain mAb 2021 a number of lower affinity variants were identified. The variants were generated as described above by site-directed mutagenesis. mAb 2007 represents such a lower affinity variants. mAb 2007 carries a single A60P back mutations in the VH domain compared to the sequence for the grafted HzTFPI4F36 (numbering according to Kabat). The variant has TFPI binding affinities that is lower by at least one order of magnitude, respectively compared to mAb 2021. The initial grafted HzTFPI4F36 variant (mAb 2000) exhibited TFPI binding affinities approximately three orders of magnitude lower compared to mAb 2021.

Expression vectors for expression of Fab fragments of mAb 2021 and mAb 2021 variants were generated as described in example 6.

Example 6: Fab Components for Bispecific Molecules

For Fab-Fab chemical conjugates, expression vector for expression of truncated HC of mAb 2021 was generated. Cloning, humanisation and expression of mAb 2021 is described in WO2010/072691, which is hereby incorporated by reference. The IgG4-based HC of mAb 2021 was truncated in the hinge region after the first cysteine residue in the human IgG4 constant region of mAb 2021 HC as seen in SEQ ID no: 23. The truncation leaves the C-terminal cysteine available for chemical conjugation. The truncated sequence was generated by using standard restriction enzyme based cloning to introduce the VH fragment of mAb 2021 HC into a linearised pTT-based toolbox vector containing the sequence of the truncated human IgG4 CH domain. The sequences of all final constructs were verified by DNA sequencing. The Fab fragment of mAb 2021 was expressed as Fab 0088, using the mAb 2021 LC vector and the truncated HC vector described above (SEQ ID NO: 24 and SEQ ID NO: 23). The LC expression vector for Fab 0088 was identical to the LC expression for mAb 2021 which was generated as described above, i.e. the VL fragment was excised by restriction enzyme digest from the GENEART cloning vector and cloned into a linearized pTT-based vector containing the sequence for a human kappa CL domain. Heavy chain expression vectors for expression of lower affinity variants of mAb 2021 were also generated. The mAb 2021 variants originate from the humanisation of mAb 2021 and are described in WO2010/072691 and Example 5. To assemble the expression vectors, the region corresponding to the VH domain of the HCs of mAb 2007 and mAb 2000 described in Example 5 were cloned using standard restriction enzyme based cloning, into a linearised pTT-based toolbox vector containing the sequence of the truncated human IgG4 CH domain. The IgG4-based HCs were truncated after the first cysteine in the IgG4 hinge, leaving the C-terminal cysteine available for chemical conjugation. The sequences of the final constructs were verified by DNA sequencing. The lower affinity Fab fragments of mAb 2007, and mAb 2000 were expressed as Fab 0094 (SEQ ID NO: 21 and SEQ ID NO: 22) and Fab 0313 (SEQ ID NO: 25 and SEQ ID NO: 26), respectively. Fab 0094 and Fab 0313 carry the same LC as Fab 0088.

Example 7a: Synthesis of 1,16-Bis(2,5-Pyrrole-dione-1-yl)-4,13-diaza-7,10-dioxa-3,14-dioxohexadecane

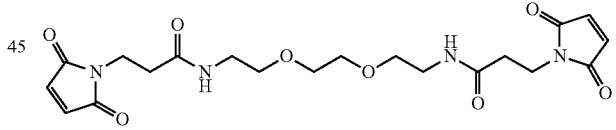

3-(2,5-pyrroledione-1-yl)propanoic acid (3.0 g, 18 mmol) was dissolved in dichloromethane (20 ml). The solution was added to pre-washed immobilised Dicyclohexylcarbodiimide resin (Novabiochem, product #8.55029.0025, batch: S5092229 036, 2.3 mmol/g, 10 g), 100 ml total volume. The mixture was stirred for 30 minutes.

A solution of 1,8-diamino-3,6-dioxaoctane (1.3 g, 8.9 mmol) in dichloromethane (50 ml) was added drop wise to the stirring solution over a period of 60 minutes. The mixture was stirred for 2 h. The solution was filtered and concentrated in vacuo to dryness. Yield: 3.4 g of a pale brownish solid.

The product was characterised by LCMS ([M+H]$^+$: 451) and NMR ($^1$H and $^{13}$C).

A fraction of the prepared material was heated to 90 degrees Celsius in acetic anhydride for 3 h. The solution was cooled, mixed with water, frozen and lyophilised.

The product was characterised by LCMS ([M+Na]$^+$: 473). This material was used for the conjugation described in the following two examples.

Example 7b: Conjugation of Fab 0088 and Fab 0295 with 1,16-Bis(2,5-Pyrroledione-1-yl)-4,13-diaza-7,10-dioxa-3,14-dioxohexadecane to Yield BiFab 9041

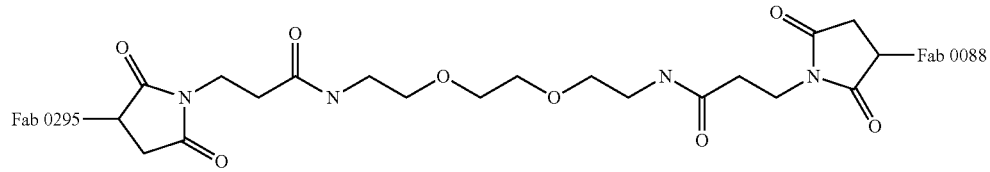

The solutions of Fab molecules (4 mg of each Fab) were adjusted to 2.5 mg/ml (50 micromolar) in phosphate buffered saline (PBS). A solution of Bis(sulfonatophenyl)phenylphosphine dipotassium dihydrate salt (CAS: 151888-20-9, Sigma-Aldrich) dissolved in PBS was added to the solution of Fab in PBS to a resulting concentration of 50 micromolar Fab and 200 micromolar of the phosphine reagent. The solutions were incubated at ambient temperature overnight.

The Fab 0088 was buffer-exchanged into 15 mM sodium acetate buffer, 1.0 M NaCl, pH 5.0 (1 ml end volume using an Amicon Ultracel Centrifugal filter (MWCO 10 kDa, Millipore A/S, Hellerup, Denmark).

The Fab 0295 was buffer-exchanged into 15 mM sodium acetate buffer, pH 4.5 using an Amicon Ultracel Centrifugal filter (MWCO 10 kDa, Millipore A/S, Hellerup, Denmark). End volume: 300 microliter.

1,16-Bis(2,5-Pyrroledione-1-yl)-4,13-diaza-7,10-dioxa-3,14-dioxohexadecane (5 mg) was added to the reduced Fab protein. The resulting mixture was incubated at room temperature for 50 minutes.

The sample was loaded onto a HiTrap SP HP column (1 ml, preconditioned in 15 mM sodium acetate buffer, pH 4.5, GE Healthcare Europe GmbH, DK-2605, Denmark). The immobilised protein was washed with 15 mM sodium acetate buffer, pH 4.5 (15 column volumes) and eluted with 15 mM sodium acetate buffer, 1 M NaCl, pH 5.0. The two protein solutions were mixed and concentrated using Amicon Ultracel Centrifugal filter (MWCO 10 kDa, MWCO 10 kDa, Millipore A/S, Hellerup, Denmark). End volume: 100 microliter.

The mixture was incubated at ambient temperature for 20 hours. The solution was loaded onto a Superdex200 16/60 column (GE Healthcare Europe GmbH, DK-2605, Denmark) that had been preconditioned in 10 mM HEPES, 150 mM NaCl, pH 7.3. The compound BiFab 9041 was eluded using said buffer. The selected fractions were pooled, concentrated and analysed using SDS-PAGE analysis, SEC-MALS, LCMS and Edman sequence determination.

The solutions of Fab molecules (5 mg of Fab 0313 and 7 mg of Fab 0295) were adjusted to 2.5 mg/ml (50 micromolar) in phosphate buffered saline (PBS). A solution of Bis(sulfonatophenyl)phenylphosphine dipotassium dihydrate salt (CAS no.: 151888-20-9, Sigma-Aldrich) dissolved in PBS was added to the solution of Fab in PBS to a resulting concentration of 50 micromolar Fab and 200 micromolar of the phosphine reagent. The solutions were incubated at ambient temperature overnight.

The Fab 0313 was buffer-exchanged into 15 mM sodium acetate buffer, 1.0 M NaCl, pH 5.0 (1 ml end volume using an Amicon Ultracel Centrifugal filter (MWCO 10 kDa, Millipore A/S, Hellerup, Denmark).

The Fab 0295 was buffer-exchanged into 15 mM sodium acetate buffer, pH 4.5 using an Amicon Ultracel Centrifugal filter (MWCO 10 kDa, Millipore A/S, Hellerup, Denmark). End volume: 300 microliter.

1,16-Bis(2,5-Pyrroledione-1-yl)-4,13-diaza-7,10-dioxa-3,14-dioxohexadecane (5 mg) was added to the reduced Fab protein. The resulting mixture was incubated at room temperature for 50 minutes.

The sample was loaded onto a HiTrap SP HP column (1 ml, preconditioned in 15 mM sodium acetate buffer, pH 4.5, GE Healthcare Europe GmbH, DK-2605, Denmark). The immobilised protein was washed with 15 mM sodium acetate buffer, pH 4.5 (15 column volumes) and eluted with 15 mM sodium acetate buffer, 1 M NaCl, pH 5.0.

The two protein solutions were mixed and concentrated using Amicon Ultracel Centrifugal filter (MWCO 10 kDa, MWCO 10 kDa, Millipore A/S, Hellerup, Denmark). End volume: 100 microliter.

The mixture was incubated at ambient temperature for 20 hours. The solution was loaded onto a Superdex200 16/60 column (GE Healthcare Europe GmbH, DK-2605, Denmark) that had been preconditioned in 10 mM HEPES, 150 mM NaCl, pH 7.3. The BiFab 9042 compound was eluted using said buffer. The selected fractions were pooled, concentrated and analysed using SDS-PAGE analysis, SEC-MALS, and LCMS.

Example 8: Binding Interaction Analysis

Binding studies were performed on a Biacore T200 (GE-Healthcare) that measures molecular interactions in real time through surface plasmon resonance. Experiments were run Example 7c: Conjugation of Fab 0313 and Fab 0295 with 1,16-Bis(2,5-Pyrroledione-1-yl)-4,13-diaza-7,10-dioxa-3,14-dioxohexadecane to Yield BIFAab 9042

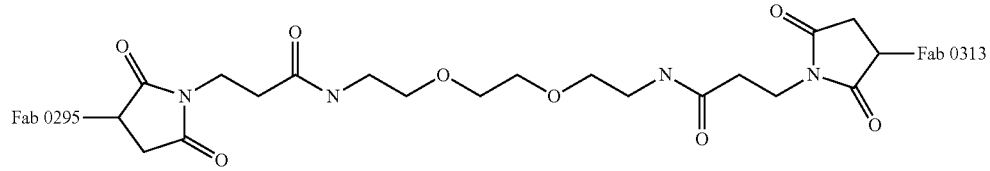

at 25° C. and the samples were stored at 15° C. in the sample compartment. The signal (RU, response units) reported by the Biacore is directly correlated to the mass on the individual sensor chip surfaces in four serial flow cells. Goat anti Fab Kappa Light Chain antibody (Nordic Biosite) was immobilized onto all four flow cells of a CM4 sensor chip according to the manufacturer's instructions. Capture of purified bispecific molecules was conducted by diluting the proteins into running buffer (10 mM Hepes 0.3 M NaCl, 5 mM $CaCl_2$, 0.05% surfactant P20, 10 mg/ml BSA, pH 7.4) and injected over flowcell 2, 3 or 4, creating a reference surface in flow cell 1 with only anti-Fab antibody immobilized. Bispecific molecules were either bispecific mAb 0421 (SEQ ID NOs: 27, 28 and 15, 29) or BiFab 9041 (SEQ ID NOs: 15, 18, 23, 24). Binding of TFPI FL (SEQ ID NO: 1), TFPI (1-79), and TFPI KPI-2 proteins was conducted by injecting analyte (antigen) over all flow cells to allow for comparative analyses of binding to different captured bispecific molecules relative to binding to the reference surface. The TFPI (1-79) fragment spans the N-terminal and KPI-1 domain of TFPI with an N-terminally attached GSSGSSG tag (SEQ ID NO: 16). The TFPI KPI-2 fragment spans the KPI-2 domain of TFPI with a C-terminal $HIS_6$ tag (SEQ ID NO: 3). Antigens were diluted serially into running buffer, injected at 30 µl/min for 240 s and allowed to dissociate for 600 s or 14000 s. Prolonging the monitoring of dissociation phase for antigens that dissociates slowly with $k_d$ approaching 1E-5 $s^{-1}$ is crucial to get a robust value for the dissociation rate. The CM4 surface was regenerated after each injection cycle of analyte via injection of 10 mM Glycine, pH 2.1. This regeneration step removed the anti-TFPI bispecific molecule and any bound antigen from the immobilized capture antibody surface, and allowed for the subsequent binding of the next interaction sample pair. The regeneration procedure did not remove the directly immobilized anti-Fab capture antibody from the chip surface.

Binding affinity between a BiFab or a bispecific mAb and the antigen was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by global fitting data to 1:1 Langmuir model with local Rmax using the Biacore evaluation software for data analysis. $K_D$ is related to $k_a$ and $k_d$ through the equation $K_D = k_d / k_a$.

Binding curves were processed by double referencing (subtraction of reference surface signals as well as blank buffer injections over captured bispecific molecules prior to data analysis). This allowed correction for instrument noise, bulk shift and drift during sample injections.

TABLE 3

Interaction kinetics for TFPI proteins binding to bispecific molecules Results from measurements of binding constants $k_a$ (association rate), $k_d$ (dissociation rate) and $K_D$ (equilibrium dissociation constant) for the interaction of human TFPI (1-79) or KPI-2 to different bispecific molecules.

| Bispecific antibody | Description | Antigen | $k_a$ (1/(Ms)) | $k_d$ (1/s) | $K_D$ (M) |
|---|---|---|---|---|---|
| BiFab 9041 | Anti KPI-1-Anti KPI-2 | TFPI (1-79) | 3E+05 | 3E−04 | 9E−10 |
| BiFab 9041 | Anti KPI-1-Anti KPI-2 | TFPI KPI-2 | 4E+06 | 6E−05 | 1E−11 |
| mAb 0421 | Anti KPI-1-Anti KPI-2 | TFPI (1-79) | 4E+05 | 1E−04 | 3E−10 |
| mAb 0421 | Anti KPI-1-Anti KPI-2 | TFPI KPI-2 | 5E+06 | 8E−05 | 2E−11 |

Figure 3:
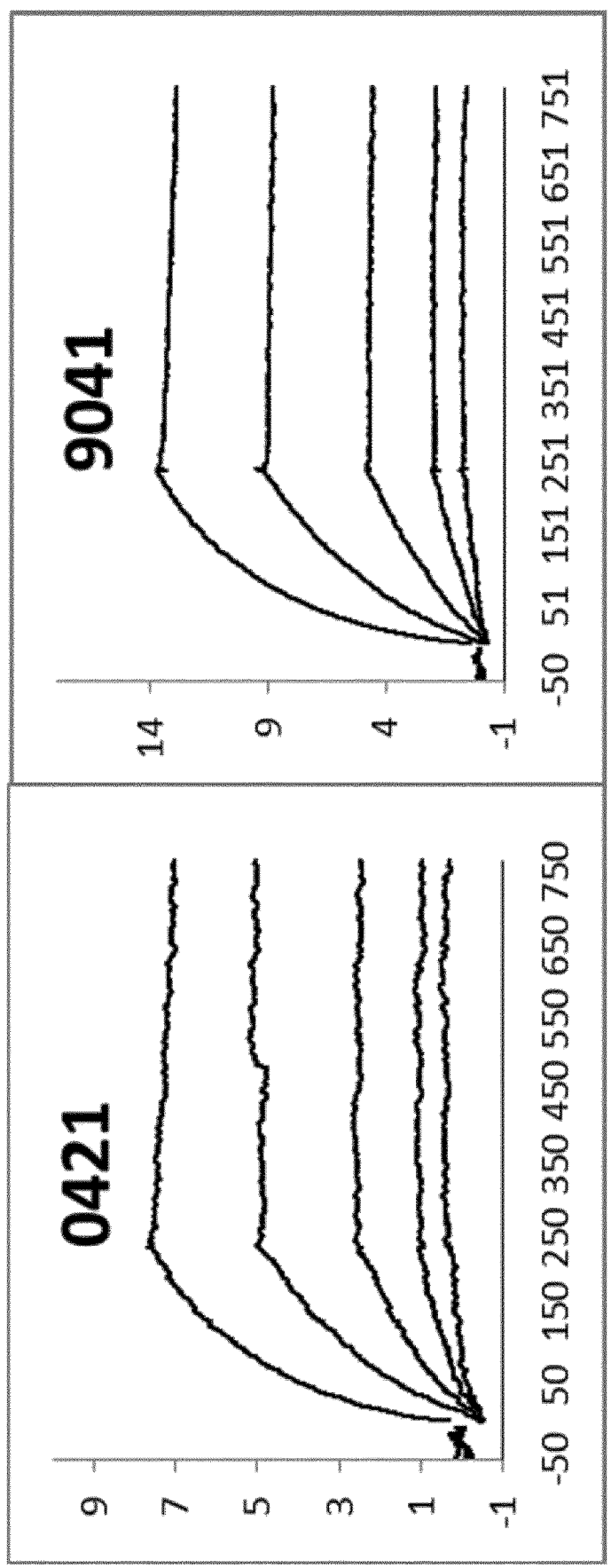
FIG. 3: Results from TFPI FL binding to captured bispecific antibody mAb 0421 and BiFab 9041.

No large differences in BiFab 9041 and mAb 0421 were found in binding of TFPI (1-79) and TFPI KPI-2 binding (Table 3). Binding of TFPI FL show a different binding profile, compared to the single TFPI domains, to both bispecific molecules in that binding appear to be influenced by multivalent or avidity binding even at low ligand densities giving rise to a higher apparent affinity. TFPI FL binding to mAb 0421 and BiFab 9041 has similar binding curve shapes demonstrating that by introducing bispecific binding by chemical conjugation of two antibody fragments like in the BiFab used in this example, the same effect on binding profile is achieved as for a bispecific antibody (cf. FIG. 3).

Example 9: Thrombin Generation Assay

The effect of antibodies on thrombin generation was studied in normal human plasma (CryoCheck Normal Plasma). Initiation of coagulation was induced by re-calcification and addition of 1 pM tissue factor with 4 µM phospholipid vesicles (PPP-Reagent low). Haemophilia A-like plasma was obtained by the addition of 100 µg/ml sheep anti-human FVIII antibody (Haematologic Technologies Inc., PAHFVIII-S). When indicated 10-20 nM exogenous recombinant human TFPIα (SEQ ID NO: 1) was added to the plasma. Thrombin activity was assessed continuously following the conversion of the fluorogenic substrate Z-Gly-Gly-Arg-AMC.HCl (1-1140) from Bachem (Bubendorf, Switzerland). Fluorescence was measured in a microtiter plate Fluorskan Ascent fluorometer (Thermo Labsystems, Helsinki, Finland) with excitation and emission wavelengths set at 368 and 460 nm, respectively. A calibrator was used to allow calculation of the amount of thrombin formed and correction of the obtained relative fluorescence units for inner-filter effects and fluorogenic substrate consumption. In addition, the contribution to substrate conversion by thrombin-α2-macroglobulin complexes was subtracted. These corrections were performed automatically by means of the calibrated automated thrombogram (CAT) computer software provided by Thrombinoscope BV (Maastricht, the Netherlands). The first derivative of the data was taken that yielded the thrombin generation curve, allowing calculation of i) lag time, ii) total area under the curve, the endogenous thrombin potential (ETP), iii) thrombin peak height (Peak), iv) time to peak (ttPeak) and v) maximal rate of thrombin generation (Rate).

Example 10: Effect of Anti-TFPI Antibodies Specific for TFPI (1-161) on Tissue Factor-Induced Thrombin Generation in Human FVIII-Neutralised Plasma with Elevated TFPIα Levels The effect of anti-TFPI (1-79) antibodies mAb 1F91, mAb 2F22, mAb 2F45 and mAb 2F3 and TFPI KPI-2 antibody mAb 2021 on thrombin generation was studied in a thrombin generation assay according to example 9 (FIG. 1).

Parameters from the thrombin generation in FIG. 1 can be seen in Table 4. The time to peak (ttPeak, min) and thrombin peak (nM) are all mean of n=3. 200 nM of antibodies was added to FVIII neutralised plasma supplemented with 20 nM TFPIα.

TABLE 4

Thrombin peak height (Peak) and time to peak (ttPeak)
Thrombin peak height (Peak) and time to peak (ttPeak) derived from thrombin generation curves obtained in FVIII-neutralised plasma supplemented with 20 nM TFPIα

| TFPI (nM) | Antibody (200 nM) | Peak (nM) | ttPeak (min) |
|---|---|---|---|
| FVIII neutralised plasma | | | |
| 20 | mAb 1F91 | 0.0 | n.a |
| 20 | mAb 2F3 | 20.9 | 14.6 |
| 20 | mAb 2F22 | 23.7 | 13.6 |
| 20 | mAb 2F45 | 7.2 | 23.6 |
| 20 | mAb 2021 | 17.2 | 26.2 |
| 20 | — | 0 | n.a |
| Normal plasma | | 71 | 11.6 |

Some, but not all, high affinity TFPI (1-79) antibodies were capable of a partial restoration of thrombin generation in haemophilia A-like plasma with 20 nM TFPIα. The data in Table 4 suggest that a more efficient blockage of TFPI inhibition is needed when the presence of TFPI antibodies in the circulation results in accumulation and an increase in the plasma TFPI concentration.

Figure 2:
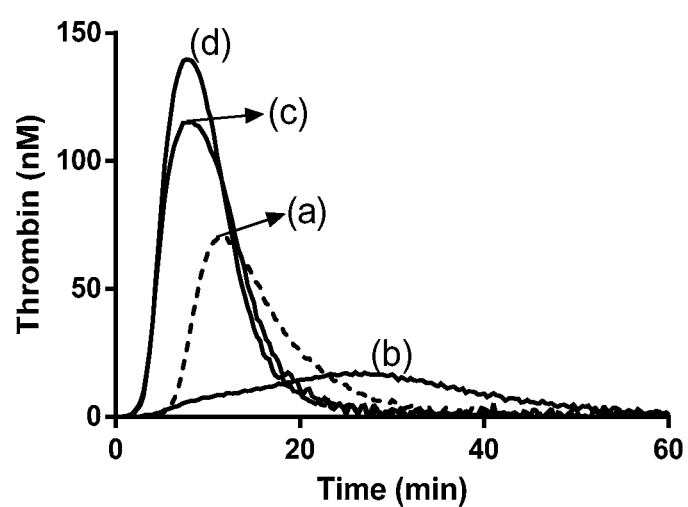
FIG. 2: Thrombin generation is strongly enhanced by combining TFPI (1-79) and TFPI-KPI-2 antibodies in human plasma under haemophilia A-like conditions with increased TFPI levels. Curve (a) shows the result obtained in normal human plasma without further additions. Curve (b) shows the result when haemophilia A-like conditions are obtained by the addition of 100 µg/ml FVIII antibody (HTI PAHFVIII-S), 20 nM TFPIα and 200 nM KPI-2 antibody, mAb 2021. The incomplete neutralisation in (b) with 200 nM mAb 2021 was reversed by combining 100 nM of mAb 2021 with 100 nM TFPI (1-79) antibody mAb 1F91 (c) or mAb 2F22 (d). The combinations of TFPI (1-79) and KPI-2 antibodies in (c) and (d) resulted in higher thrombin peaks than normal human plasma (a).

The effect of combining each of the anti-TFPI (1-79) antibodies with anti-TFPI KPI-2 mAb 2021 on thrombin generation was studied in a thrombin generation assay according to example 9 and illustrated in FIG. 2. Parameters from the thrombin generation in FIG. 2 can be seen in Table 5. The time to peak (ttPeak, min) and thrombin peak (nM) are all mean of n=3. 100 nM of antibodies was added to FVIII neutralised plasma supplemented with 20 nM TFPIα and 100 nM mAb 2021.

TABLE 5

Thrombin peak height (Peak) and time to peak (ttPeak)
Thrombin peak height (Peak) and time to peak (ttPeak) derived from thrombin generation curves obtained in FVIII-neutralised plasma supplemented with 20 nM TFPIα. 100 nM of each antibody was added to the plasma.

| TFPI (nM) | Antibody (100 nM) | Peak (nM) | ttPeak (min) |
|---|---|---|---|
| FVIII neutralised plasma | | | |
| 20 | mAb 1F91 + mAb 2021 | 116.2 | 8.1 |
| 20 | mAb 2F3 + mAb 2021 | 139.0 | 7.7 |
| 20 | mAb 2F22 + mAb 2021 | 140.3 | 7.9 |
| 20 | mAb 2F45 + mAb 2021 | 139.9 | 7.8 |
| 20 | mAb 2021 + mAb 2021 | 17.2 | 26.2 |
| 20 | — | 0 | n.a |
| Normal plasma | | 71 | 11.6 |

The data in Table 5 suggest that a more efficient blockage of TFPI inhibition is obtained by neutralisation of more than one epitope involved in stabilization of the TF/FVIIa/FXa/TFPI complex.

Example 11: Synergistic Effect of Anti-TFPI BiFabs on Tissue Factor-Induced Thrombin Generation in Human Haemophilia A Plasma Fab fragments against TFPI (1-79), the KPI-2 domain of TFPI and BiFabs were prepared according to examples 2 and 5-7. The effect on thrombin generation of BiFab targeting TFPI (1-79) and the KPI-2 domain were compared to the effect of the corresponding non-conjugated Fab fragments alone or in combination. The effect on thrombin generation in FVIII-neutralised plasma and in FVIII-neutralised plasma supplemented with 10 nM TFPIα was measured according to Example 9 and the data are listed in Table 6. Parameters were derived from thrombin generation curves. The time to peak (ttPeak, min) and thrombin peak (nM) are all mean of n=2.

TABLE 6

Thrombin peak height (Peak) and time to peak (ttPeak)
Thrombin peak height (Peak) and time to peak (ttPeak) derived from thrombin generation curves obtained in FVIII-neutralised plasma with endogenous TFPI levels or supplemented with 10 nM TFPIα. When a combination of FAb fragments was used, each was added to a concentration of 100 nM.

| FVIII neutralised plasma | | Peak (nM) | | | | | | |
|---|---|---|---|---|---|---|---|---|
| TFPI (nM) | FAb/BiFab (nM) | 0295 | 0088 | 0313 | 0295 + 0088 | 9041 | 0295 + 0313 | 9042 |
| 10 | 100 | 33.8 | 54.2 | 1.4 | 131.7 | 130.7 | 62.9 | 115.1 |
| 10 | 50 | 31.8 | 42.9 | 0.8 | 129.9 | 132.0 | 46.4 | 109.6 |
| 10 | 10 | 10.9 | 12.7 | 0.4 | 48.3 | 56.1 | 10.3 | 55.0 |
| 10 | 0 | 0.4 | 0.4 | 0.4 | 0.4 | 0.4 | 0.4 | 0.4 |
| 0 | 100 | 103.4 | 90.2 | 29.6 | 138.1 | 131.7 | 125.7 | 134.3 |
| 0 | 50 | 101.4 | 85.2 | 19.8 | 139.8 | 137.0 | 115.1 | 135.5 |
| 0 | 10 | 94.0 | 85.6 | 10.0 | 137.5 | 135.5 | 93.7 | 129.1 |
| 0 | 0 | 8.6 | 8.6 | 8.6 | 8.6 | 8.6 | 8.6 | 8.6 |
| Normal plasma | | Peak (nM) 49.6 | | | | | | |

| FVIII neutralised plasma | | ttPeak (min) | | | | | | |
|---|---|---|---|---|---|---|---|---|
| TFPI (nM) | FAb/BiFab (nM) | 0295 | 0088 | 0313 | 0295 + 0088 | 9041 | 0295 + 0313 | 9042 |
| 10 | 100 | 10.8 | 20.2 | 48.1 | 7.7 | 8.0 | 7.9 | 7.8 |
| 10 | 50 | 11.5 | 21.2 | 76.2 | 7.8 | 7.8 | 8.8 | 7.9 |
| 10 | 10 | 25.2 | 29.0 | 105.8 | 13.8 | 11.6 | 25.2 | 9.2 |
| 10 | 0 | 97.6 | 97.6 | 97.6 | 97.6 | 97.6 | 97.6 | 97.6 |

TABLE 6-continued

Thrombin peak height (Peak) and time to peak (ttPeak)
Thrombin peak height (Peak) and time to peak (ttPeak) derived from thrombin
generation curves obtained in FVIII-neutralised plasma with endogenous TFPI
levels or supplemented with 10 nM TFPIα. When a combination of FAb fragments
was used, each was added to a concentration of 100 nM.

| 0 | 100 | 8.2 | 11.6 | 8.9 | 7.8 | 7.9 | 7.5 | 7.8 |
|---|---|---|---|---|---|---|---|---|
| 0 | 50 | 8.2 | 11.6 | 10.2 | 7.8 | 7.8 | 7.7 | 7.7 |
| 0 | 10 | 8.4 | 11.5 | 21.0 | 78 | 7.6 | 8.3 | 8.1 |
| 0 | 0 | 23.0 | 23.0 | 23.0 | 23.0 | 23.0 | 23.0 | 23.0 |

| Normal plasma | ttPeak (min) |
|---|---|
| | 12.3 |

The data in Table 6 suggest that a more efficient blockage of TFPI inhibition is obtained by neutralisation of more than one epitope on TFPI. It clearly follows that the high affinity obtained due to an avidity effect (Example 8) for BiFab 9042 binding to TFPI, results in a synergistic effect on thrombin generation which is higher than the effect obtained by combining the corresponding two non-conjugated Fab fragments.

Example 12: Effect of Anti-TFPI Bispecific Antibodies on Tissue Factor-Induced Thrombin Generation in Human Haemophilia A Plasma A pro-coagulant effect on tissue factor-induced thrombin generation in human haemophilia A plasma can be obtained by using an asymmetric bispecific antibody, assembled through Fc heterodimerisation of antibodies targeting epitopes in the TFPI (1-79) and the KPI-2 regions of TFPI. Generation of Asymmetric Bispecific Antibodies A bispecific TFPI (1-79)/KPI-2 binding antibody was generated based on an asymmetric IgG format, i.e. through Fc heterodimerisation. In order to achieve FC heterodimerisation a set of compatible mutations were engineered into the Fc region of hIgG1 variants of mAb 2021 (KPI-2 binding) and mAb 2F22 (TFPI (1-79) binding).

The VH fragments were excised from the HC expression vector for humanized mAb 2021 described in Example 5 and the HC expression vector mAb 2F22 expressions vectors by restriction enzyme digestion and cloned into a linearized pTT-based toolbox vector containing the sequence for a human IgG1 constant region. The cloning reaction was subsequently transformed into E. coli for selection. The sequence of the final construct was verified by DNA sequencing.

To support FC heterodimerisation by controlled Fab-arm exchange, a single lysine to arginine mutation was introduced into the CH3 domain of the IgG1 HC of mAb 2021, corresponding to position 413 in SEQ ID NO: 27. The mutation was introduced by site-directed mutagenesis using the QuikChange® Site-Directed mutagenesis kit from Stratagene.

The sequences of all final construct were verified by DNA sequencing. The engineered IgG1 version of mAb 2021 was expressed as mAb 0310 (SEQ ID NOs 27 and 28) in EXP1293F cells as described in Example 2. The LC expression vector corresponds to the vector used for expression of mAb 2021 as described in Example 5. Purification was performed by standard affinity chromatography using MabSelectSuRe resin from GE Healthcare according to manufacturer's instructions. The purified antibodies were buffer exchanged to PBS buffer pH 7.2.

A matching phenylalanine to leucine mutation was introduced into the CH3 domain of the IgG1 HC of mAb 2F22, corresponding to position 409 in SEQ ID NO: 29. The mutation was introduced by site-directed mutagenesis using the QuikChange® Site-Directed mutagenesis kit from Stratagene. The sequences of all final construct were verified by DNA sequencing. The engineered IgG1 version of mAb 2F22 was expressed as mAb 0336 (SEQ ID NOs: 15 and 29) in EXP1293F cells as described in Example 2. The LC expression vector corresponds to the vector used for expression of mAb 2F22 as described in Example 2. Purification was performed by standard affinity chromatography using MabSelectSuRe resin from GE Healthcare according to manufacturer's instructions. The purified antibodies were buffer exchanged to PBS buffer pH 7.2.

A bispecific TFPI (1-79)/KPI-2 binding antibody was prepared by controlled Fab-arm exchange between the engineered IgG1 variant of mAb2021 (KPI-2 binding), mAb 0310 and the engineered IgG1 variant of mAb 2F22 (TFPI (1-79) binding), mAb 0336. The bispecific antibody was prepared essentially according to published methods (Labrijn et al., PNAS, 110, 5145-5150 (2013)). In short, mAb 0310 (mAb 2021 IgG1 Lys-to-Arg variant SEQ ID NO: 27) was mixed with mAb 0336 (mAb 2F22 IgG1 Phe-to-Leu variant SEQ ID NO: 29) at a 1:1 molar ratio (1 mg/ml per antibody) in PBS buffer. The antibodies were selectively reduced by incubation of the 1:1 mixture for 90 minutes at 37° C. in the presence of 25 mM 2-mercaptoethylamine (MEA) to form half antibodies and allow Fab-arm exchange. Finally, spontaneous reassembly and re-oxidation was obtained after removal of the reducing agent (diafiltration in to PBS buffer without MEA) and storage at +5° C. for at least 16 hours. Hetero-dimerisation, promoted by the CH3 domain mutations, was observed with an efficiency exceeding 90%. The final bispecific antibody derived from mAb 0310 and 0336 was named mAb 0421 (SEQ ID NOs: 27, 28 and 15, 29).

Effect of Anti-TFPI Bispecific Antibodies on Tissue Factor-Induced Thrombin Generation in Human Haemophilia A Plasma A pro-coagulant effect on tissue factor-induced thrombin generation in human haemophilia A plasma can be obtained by using an asymmetric bispecific antibody, assembled through Fc heterodimerisation of antibodies targeting epitopes in the TFPI (1-79) and the KPI-2 regions of TFPI. The effect on thrombin generation in FVIII-neutralised plasma and in FVIII-neutralised plasma supplemented with 10 nM TFPI alpha was studied in a thrombin generation assay according to Example 9 and the data are listed in Table 7. Parameters were derived from thrombin generation curves.

TABLE 7

Thrombin peak height (Peak) and time to peak (ttPeak)

| FVIII-neutralized plasma | | Peak (nM) | | | ttPeak (min) | | |
|---|---|---|---|---|---|---|---|
| TFPI (nM) | mAb (nM) | 0421 | 0336 | 0310 | 0421 | 0336 | 0310 |
| 0 | 10.0 | 181.5 | 140.1 | 118.1 | 6.9 | 7.8 | 8.5 |
| 0 | 5.0 | 177.3 | | | 7.2 | | |
| 0 | 2.5 | 167.1 | | | 7.3 | | |
| 0 | 1.3 | 98.7 | | | 8.5 | | |
| 0 | 0.6 | 32.0 | | | 10.3 | | |
| 0 | 0.3 | 17.4 | | | 14.8 | | |
| 0 | 0.2 | 13.3 | | | 17.9 | | |
| 0 | 0.0 | 12.4 | | | 17.9 | | |
| 10 | 100.0 | 177.0 | 44.9 | 28.3 | 7.0 | 11.7 | 24.5 |
| 10 | 50.0 | 175.0 | | | 7.3 | | |
| 10 | 25.0 | 169.2 | | | 7.3 | | |
| 10 | 12.5 | 162.6 | | | 7.7 | | |
| 10 | 6.3 | 7.7 | | | 8.8 | | |
| 10 | 3.1 | 0.0 | | | 0.0 | | |
| 10 | 1.6 | 0.0 | | | 0.0 | | |
| 10 | 0.0 | 0.0 | | | 0.0 | | |
| Normal plasma | | 94.1 | | | 10.7 | | |

Table 7 shows that the addition of anti-human FVIII antibody to normal plasma to simulate haemophilia A-like condition strongly reduced thrombin generation. Both the thrombin peak (Peak) and the time to peak (ttPeak) were affected. Addition of a number of anti-TFPI antibodies, including mAb 0310 (an Fc engineered version of mAb 2021), mAb 0336 (an Fc engineered version of anti-TFPI mAb 2F22) and mAb 0421 (the asymmetric bispecific antibody derived from mAb 0310 and mAb 0336) to FVIII-neutralised plasma efficiently re-establishes both thrombin peak (Peak) and time to peak (ttPeak). The mAb 0421 concentration required to give half-maximal response (EC50) was estimated to be 1.1 nM (the data, average of 2 experiments, given in table 7 was fitted to a four-parameter dose-response curve using the GraphPad PrismR software).

Moreover, table 7 shows that addition of 10 nM full-length TFPI alpha to FVIII-neutralised plasma completely prevented a measurable thrombin generation and that addition of 100 nM of a high affinity antibody against TFPI (1-79) (mAb 0336) or KPI-2 (mAb 0310) could not completely abrogate TFPI inhibition under these conditions. In contrast, the asymmetric bispecific antibody mAb 0421 dose dependently established a robust thrombin peak and reduced time to peak (ttPeak) with an estimated EC50 of 9.5 nM (single experiment).

The data in Table 7 suggest that a more efficient blockage of TFPI inhibition is obtained by neutralization of more than one epitope on TFPI.

Example 13: Bispecific Molecules Binding with High Affinity to TFPI KPI-2 and with Low Affinity for TFPI KPI-1

For certain applications of bispecific TFPI (1-79)/KPI-2 binding molecules it may be advantageous to have high-affinity binding to TFPI KPI-2 with one arm and low affinity TFPI TFPI (1-79) binding with the other.

Fab 0296 (SEQ ID NOs: 14 (heavy chain) and 15 (light chain)), corresponding to mAb 2F22, binds with high affinity to TFPI (1-79), an can serve as a template for designing variants with reduced affinity for TFPI (1-79), as compared with Fab 0296.

As described in Example 4 the paratope for Fab 0296 has been determined and includes residues Val 2, Phe 27, Tyr 32, Trp 52, Arg 53, Gly 54, Gly 55, Ser 56, Ile 57, Asp 58, Tyr 59, Ala 61, Met 64, Lys 97, Ser 99, His 100, Asn 102, Tyr 103, Val 104, Gly 105 and Tyr 106 of the heavy chain (SEQ ID NO: 14), and residues Pro 31, Ala 32, Tyr 49, Ser 50, Asn 53, Tyr 55, Thr 56, Tyr 91, Thr 92, Ser 93 and Tyr 94 of the light chain (SEQ ID NO: 15).

The high affinity of Fab 0296 results from a combination of several interactions, e.g. electrostatic, polar, hydrophobic and hydrogen bond interactions, between its paratope residues, mentioned above, and the epitope residues on TFPI (1-79). Thus, the binding affinity of Fab 0296 for TFPI (1-79) is modulated by substituting one or more of the paratope residues with a different amino acid residue, thereby weakening or strengthening paratope-epitope interactions.

The affinity of Fab 0296 for TFPI (1-79) is attenuated to different degrees by e.g. a conservative substitution at a single position, a conservative substitution at several positions, or less conservative substitutions at one or more positions.

Fab 0295 (SEQ ID NOs: 18 (heavy chain) and 15 (light chain)), is identical to Fab 0296 save for an additional cysteine at the C-terminus of the heavy chain, and has the same paratope as Fab 0296. A bispecific TFPI (1-79)/KPI-2 binding molecule with low affinity for TFPI (1-79) is therefore prepared by using a variant of Fab 0295, where a single or more paratope residues have been substituted, and conjugating it to a KPI-2 binding Fab, as described in Example 7. The KPI-2 binding Fab may e.g. be Fab 0088 but can also be other KPI-2 binding Fab fragments.

By using full length antibodies corresponding to the Fab fragments described in this example it is possible to obtain corresponding bispecific antibodies according to methods described in example 12.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A bispecific antibody capable of specifically binding a first epitope within positions 1-76 and a second epitope within positions 77-161 of human Tissue Factor Pathway Inhibitor (TFPI) (SEQ ID NO:1),
wherein the heavy chain of the first antigen recognition site comprises:
a complementary determining region (CDR) 1 sequence corresponding to amino acids 31 to 35 of SEQ ID NO: 6 (NYGVH); and
a CDR2 sequence corresponding to amino acids 50 to 65 of SEQ ID NO: 6 (VIWRGGSIDYNAAFMS); and
a CDR3 sequence corresponding to amino acids 98 to 110 of SEQ ID NO: 6 (NSHGNYVGYAMDY); and
wherein the light chain of the first antigen recognition site comprises:
a CDR1 sequence corresponding to amino acids 24 to 34 of SEQ ID NO: 7 (KASQSVGPAVA); and
a CDR2 sequence corresponding to amino acids 50 to 56 of SEQ ID NO: 7 (SASNRYT); and
a CDR3 sequence corresponding to amino acids 89 to 96 of SEQ ID NO: 7 (QQYTSYPT); and
wherein the heavy chain of the second antigen recognition site comprises:
a CDR1 sequence corresponding to amino acids 31 to 35 (NYAMS) of SEQ ID NO:19; and
a CDR2 sequence corresponding to amino acids 50 to 66 SEQ ID NO: 25 (TISRSGSYSYYADSVKG); and
a CDR3 sequence corresponding to amino acids 99 to 110 (LGGYDEGDAMDS) of SEQ ID NO:19; and
wherein the light chain of the second antigen recognition site comprises:
a CDR1 sequence corresponding to amino acids 24 to 39 (KSSQSLLESDGKTYLN) of SEQ ID NO: 20; and
a CDR2 sequence corresponding to amino acids 55 to 61 (LVSILDS) of SEQ ID NO: 20; and
a CDR3 sequence corresponding to amino acids 94 to 102 (LQATHFPQT) of SEQ ID NO: 20.

2. The bispecific antibody according to claim 1, wherein the bispecific antibody is a bispecific Fab-Fab conjugate (BiFab).

3. A method of treating a coagulopathy in a subject in need thereof comprising administering the bispecific antibody according to claim 1 to said subject.

4. The method of claim 3, wherein the coagulopathy is haemophilia A or B, with or without inhibitors.

5. The bispecific antibody of claim 1, which is humanized or human.

6. The bispecific antibody of claim 1, which is a full-length bispecific antibody or a chemical conjugate of two antigen binding fragments.

* * * * *

SEQUENCE LISTING

<160> NUMBER OF SEQ ID NOS: 29

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu

```
           1               5                  10                 15
       Pro Pro Leu Lys Leu Met His Ser Phe Cys Ala Phe Lys Ala Asp Asp
                       20                 25                 30

Gly Pro Cys Lys Ala Ile Met Lys Arg Phe Phe Asn Ile Phe Thr
                   35                 40                 45

Arg Gln Cys Glu Glu Phe Ile Tyr Gly Gly Cys Gly Asn Gln Asn
                   50                 55                 60

Arg Phe Glu Ser Leu Glu Glu Cys Lys Lys Met Cys Thr Arg Asp Asn
       65                  70                 75                 80

Ala Asn Arg Ile Ile Lys Thr Thr Leu Gln Gln Glu Lys Pro Asp Phe
                       85                 90                 95

Cys Phe Leu Glu Glu Asp Pro Gly Ile Cys Arg Gly Tyr Ile Thr Arg
                       100                105                110

Tyr Phe Tyr Asn Asn Gln Thr Lys Gln Cys Glu Arg Phe Lys Tyr Gly
                       115                120                125

Gly Cys Leu Gly Asn Met Asn Asn Phe Glu Thr Leu Glu Glu Cys Lys
                   130                135                140

Asn Ile Cys Glu Asp Gly Pro Asn Gly Phe Gln Val Asp Asn Tyr Gly
       145                 150                155                160

Thr Gln Leu Asn Ala Val Asn Asn Ser Leu Thr Pro Gln Ser Thr Lys
                       165                170                175

Val Pro Ser Leu Phe Glu Phe His Gly Pro Ser Trp Cys Leu Thr Pro
                   180                185                190

Ala Asp Arg Gly Leu Cys Arg Ala Asn Glu Asn Arg Phe Tyr Tyr Asn
                   195                200                205

Ser Val Ile Gly Lys Cys Arg Pro Phe Lys Tyr Ser Gly Cys Gly Gly
                   210                215                220

Asn Glu Asn Asn Phe Thr Ser Lys Gln Glu Cys Leu Arg Ala Cys Lys
       225                 230                235                240

Lys Gly Phe Ile Gln Arg Ile Ser Lys Gly Gly Leu Ile Lys Thr Lys
                       245                250                255

Arg Lys Arg Lys Lys Gln Arg Val Lys Ile Ala Tyr Glu Glu Ile Phe
                       260                265                270

Val Lys Asn Met
                       275

<210> SEQ ID NO 2
<211> LENGTH: 161
<212> TYPE: PRT
<213> ORGANISM: Artificial sequence
<220> FEATURE:
<223> OTHER INFORMATION: TFPI (1-161)

<400> SEQUENCE: 2

Asp Ser Glu Glu Asp Glu Glu His Thr Ile Ile Thr Asp Thr Glu Leu
       1                   5                  10                 15

Pro Pro Leu Lys Leu Met His Ser Phe Cys Ala Phe Lys Ala Asp Asp
                       20                 25                 30

Gly Pro Cys Lys Ala Ile Met Lys Arg Phe Phe Asn Ile Phe Thr
                   35                 40                 45

Arg Gln Cys Glu Glu Phe Ile Tyr Gly Gly Cys Gly Asn Gln Asn
                   50                 55                 60

Arg Phe Glu Ser Leu Glu Glu Cys Lys Lys Met Cys Thr Arg Asp Asn
       65                  70                 75                 80

Ala Asn Arg Ile Ile Lys Thr Thr Leu Gln Gln Glu Lys Pro Asp Phe
```

```
                    85                  90                  95
Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr

<210> SEQ ID NO 3
<211> LENGTH: 66
<212> TYPE: PRT
<213> ORGANISM: Artificial sequence
<220> FEATURE:
<223> OTHER INFORMATION: TFPI KPI-2 construct

<400> SEQUENCE: 3

Gln Glu Lys Pro Asp Phe Cys Phe Leu Glu Glu Asp Pro Gly Ile Cys
1               5                   10                  15

Arg Gly Tyr Ile Thr Arg Tyr Phe Tyr Asn Asn Gln Thr Lys Gln Cys
            20                  25                  30

Glu Arg Phe Lys Tyr Gly Gly Cys Leu Gly Asn Met Asn Asn Phe Glu
        35                  40                  45

Thr Leu Glu Glu Cys Lys Asn Ile Cys Glu Asp Gly His His His His
    50                  55                  60

His His
65

<210> SEQ ID NO 4
<211> LENGTH: 121
<212> TYPE: PRT
<213> ORGANISM: Mus musculus

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ser Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Phe Asn Ala Ala Phe Met
    50                  55                  60

Ser Arg Val Ser Phe Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 5
<211> LENGTH: 107
<212> TYPE: PRT
<213> ORGANISM: Mus musculus
```

```
<400> SEQUENCE: 5

Asp Ile Val Met Thr Gln Ser Gln Lys Phe Met Ser Thr Thr Val Gly
1               5                   10                  15

Asp Lys Val Ser Ile Pro Cys Lys Ala Ser Glu Asn Val Gly Ala Ala
            20                  25                  30

Val Ala Trp Tyr Gln Gln Lys Pro Gly Gln Ser Pro Thr Leu Leu Ile
        35                  40                  45

Tyr Ser Ala Ser Asn Arg Tyr Thr Gly Ile Pro Asp Arg Phe Thr Gly
    50                  55                  60

Ser Gly Ser Gly Thr Asp Phe Thr Leu Thr Ile Arg Thr Val Gln Ser
65                  70                  75                  80

Glu Asp Leu Ala Asp Tyr Phe Cys Gln Gln Tyr Thr Asn Tyr Pro Thr
                85                  90                  95

Phe Gly Gly Gly Thr Lys Leu Glu Ile Lys Arg
            100                 105

<210> SEQ ID NO 6
<211> LENGTH: 121
<212> TYPE: PRT
<213> ORGANISM: Mus musculus

<400> SEQUENCE: 6

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 7
<211> LENGTH: 107
<212> TYPE: PRT
<213> ORGANISM: Mus musculus

<400> SEQUENCE: 7

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
```

Phe Gly Gly Gly Thr Lys Leu Glu Ile Lys Arg
                100                 105

<210> SEQ ID NO 8
<211> LENGTH: 121
<212> TYPE: PRT
<213> ORGANISM: Mus musculus

<400> SEQUENCE: 8

Gln Val Gln Leu Lys Gln Ser Gly Pro Gly Leu Val Gln Pro Ser Gln
1               5                   10                  15

Ser Leu Ser Ile Ser Cys Thr Val Ser Gly Phe Ser Leu Thr Gly Tyr
            20                  25                  30

Gly Val His Trp Ile Arg Gln Ser Pro Gly Lys Gly Leu Glu Trp Leu
        35                  40                  45

Gly Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser
        115                 120

<210> SEQ ID NO 9
<211> LENGTH: 107
<212> TYPE: PRT
<213> ORGANISM: Mus musculus

<400> SEQUENCE: 9

Asp Ile Val Met Thr Gln Ser Gln Lys Phe Met Ser Thr Thr Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Glu Leu Leu Ile
        35                  40                  45

Tyr Ser Ala Ser Asn Arg Tyr Thr Arg Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg
            100                 105

<210> SEQ ID NO 10
<211> LENGTH: 115
<212> TYPE: PRT
<213> ORGANISM: Mus musculus

<400> SEQUENCE: 10

Asp Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Asp
            20                  25                  30

```
        Tyr Ala Trp Asn Trp Ile Arg Gln Phe Pro Gly Asn Lys Leu Glu Trp
                     35                  40                  45

Met Gly Tyr Ile Ser Tyr Ser Gly Ser Thr Ser Tyr Asn Pro Ser Leu
             50                  55                  60

Lys Ser Arg Ile Ser Ile Thr Arg Asp Thr Ser Lys Asn Gln Phe Phe
         65                  70                  75                  80

Leu Gln Leu Asn Ser Val Thr Thr Glu Asp Thr Ala Thr Tyr Tyr Cys
                         85                  90                  95

Ala Arg Trp Ala Tyr Asp Gly Pro Trp Gly Gln Gly Thr Leu Val Thr
                    100                 105                 110

Val Ser Ala
                115

<210> SEQ ID NO 11
<211> LENGTH: 107
<212> TYPE: PRT
<213> ORGANISM: Mus musculus

<400> SEQUENCE: 11

Gln Ile Val Leu Ser Gln Ser Pro Ala Leu Leu Ser Ala Ser Pro Gly
        1               5                   10                  15

Glu Lys Val Thr Met Thr Cys Arg Ala Ser Ser Ser Val Ser His Met
                     20                  25                  30

His Trp Tyr Gln Gln Lys Pro Gly Ser Ser Pro Lys Pro Trp Ile Tyr
                     35                  40                  45

Ala Thr Ser Asn Leu Ala Ser Gly Val Pro Ala Arg Phe Ser Gly Ser
             50                  55                  60

Gly Ser Gly Thr Ser Tyr Ser Leu Thr Ile Thr Arg Val Glu Ala Glu
         65                  70                  75                  80

Asp Ala Ala Thr Tyr Tyr Cys Gln Gln Trp Ser Ser Asn Pro Phe Thr
                         85                  90                  95

Phe Gly Ser Gly Thr Lys Leu Glu Ile Lys Arg
                    100                 105

<210> SEQ ID NO 12
<211> LENGTH: 20
<212> TYPE: DNA
<213> ORGANISM: Artificial sequence
<220> FEATURE:
<223> OTHER INFORMATION: primer

<400> SEQUENCE: 12
cccttgacca ggcatcccag                                                    20

<210> SEQ ID NO 13
<211> LENGTH: 36
<212> TYPE: DNA
<213> ORGANISM: Artificial sequence
<220> FEATURE:
<223> OTHER INFORMATION: primer

<400> SEQUENCE: 13
gctctagact aacactcatt cctgttgaag ctcttg                                  36

<210> SEQ ID NO 14
<211> LENGTH: 222
<212> TYPE: PRT
<213> ORGANISM: Artificial sequence
<220> FEATURE:
<223> OTHER INFORMATION: truncated murine-human chimeric heavy chain of
```

Fab 0296

<400> SEQUENCE: 14

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys
    210                 215                 220

<210> SEQ ID NO 15
<211> LENGTH: 213
<212> TYPE: PRT
<213> ORGANISM: Artificial sequence
<220> FEATURE:
<223> OTHER INFORMATION: murine-human chimeric light chain of mAb 0294,
      Fab 0296 and Fab 0295 and mAb 0336

<400> SEQUENCE: 15

Gly Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Pro Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Ala Asp Phe Thr Leu Thr Ile Ser Asn Leu His Ser
65                  70                  75                  80

Glu Asp Leu Ala Asp Tyr Phe Cys Gln Gln Tyr Thr Ser Tyr Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr

```
            115                 120                 125
Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 16
<211> LENGTH: 86
<212> TYPE: PRT
<213> ORGANISM: Artificial sequence
<220> FEATURE:
<223> OTHER INFORMATION: tagged TFPI KPI-1/N-terminal (TFPI (1-79))

<400> SEQUENCE: 16

Gly Ser Ser Gly Ser Ser Gly Asp Ser Glu Glu Asp Glu Glu His Thr
1               5                   10                  15

Ile Ile Thr Asp Thr Glu Leu Pro Pro Leu Lys Leu Met His Ser Phe
            20                  25                  30

Cys Ala Phe Lys Ala Asp Asp Gly Pro Cys Lys Ala Ile Met Lys Arg
        35                  40                  45

Phe Phe Phe Asn Ile Phe Thr Arg Gln Cys Glu Glu Phe Ile Tyr Gly
    50                  55                  60

Gly Cys Glu Gly Asn Gln Asn Arg Phe Glu Ser Leu Glu Glu Cys Lys
65                  70                  75                  80

Lys Met Cys Thr Arg Asp
                85

<210> SEQ ID NO 17
<211> LENGTH: 448
<212> TYPE: PRT
<213> ORGANISM: Artificial sequence
<220> FEATURE:
<223> OTHER INFORMATION: murine-human chimeric heavy chain of monoclonal
      antibody mAb 0294

<400> SEQUENCE: 17

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110
```

Gln Gly Thr Ser Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 18
<211> LENGTH: 227
<212> TYPE: PRT
<213> ORGANISM: Artificial sequence
<220> FEATURE:
<223> OTHER INFORMATION: truncated murine-human chimeric heavy chain of
      Fab 0295

<400> SEQUENCE: 18

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr

```
                20                  25                  30
Gly Val His Trp Val Arg Gln Ser Pro Gly Lys Gly Leu Glu Trp Leu
             35                  40                  45

Ala Val Ile Trp Arg Gly Gly Ser Ile Asp Tyr Asn Ala Ala Phe Met
 50                  55                  60

Ser Arg Leu Ser Ile Thr Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                 85                  90                  95

Lys Asn Ser His Gly Asn Tyr Val Gly Tyr Ala Met Asp Tyr Trp Gly
                100                 105                 110

Gln Gly Thr Ser Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
        210                 215                 220

Pro Pro Cys
225

<210> SEQ ID NO 19
<211> LENGTH: 121
<212> TYPE: PRT
<213> ORGANISM: Artificial sequence
<220> FEATURE:
<223> OTHER INFORMATION: heavy chain variable domain (VH) of mAb 2021

<400> SEQUENCE: 19

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asn Tyr
             20                  25                  30

Ala Met Ser Trp Val Arg Gln Thr Pro Glu Lys Arg Leu Glu Trp Val
         35                  40                  45

Ala Thr Ile Ser Arg Ser Gly Ser Tyr Ser Tyr Phe Pro Asp Ser Val
 50                  55                  60

Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Tyr Asp Glu Gly Asp Ala Met Asp Ser Trp Gly
                100                 105                 110

Gln Gly Thr Thr Val Thr Val Ser Ser
            115                 120

<210> SEQ ID NO 20
<211> LENGTH: 113
<212> TYPE: PRT
```

<213> ORGANISM: Artificial sequence
<220> FEATURE:
<223> OTHER INFORMATION: light chain variable domain (VL) of mAb 2021

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
                100                 105                 110

Arg

<210> SEQ ID NO 21
<211> LENGTH: 227
<212> TYPE: PRT
<213> ORGANISM: Artificial sequence
<220> FEATURE:
<223> OTHER INFORMATION: heavy chain (HC) of Fab 0094

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly

```
                  210                 215                 220

Pro Pro Cys
225

<210> SEQ ID NO 22
<211> LENGTH: 219
<212> TYPE: PRT
<213> ORGANISM: Artificial sequence
<220> FEATURE:
<223> OTHER INFORMATION: light chain (LC) of Fab 0094

<400> SEQUENCE: 22

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 23
<211> LENGTH: 227
<212> TYPE: PRT
<213> ORGANISM: Artificial sequence
<220> FEATURE:
<223> OTHER INFORMATION: heavy chain (HC) of Fab 0088

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60
```

```
Gln Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys
225

<210> SEQ ID NO 24
<211> LENGTH: 219
<212> TYPE: PRT
<213> ORGANISM: Artificial sequence
<220> FEATURE:
<223> OTHER INFORMATION: light chain (LC) of Fab 0088

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Ala
                 85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 25
<211> LENGTH: 227
<212> TYPE: PRT
<213> ORGANISM: Artificial sequence
<220> FEATURE:
<223> OTHER INFORMATION: heavy chain (HC) of Fab 0313

<400> SEQUENCE: 25

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Ser Gly Ser Tyr Ser Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys
225

<210> SEQ ID NO 26
<211> LENGTH: 219
<212> TYPE: PRT
<213> ORGANISM: Artificial sequence
<220> FEATURE:
<223> OTHER INFORMATION: light chain (LC) of Fab 0313

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45
```

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 27
<211> LENGTH: 451
<212> TYPE: PRT
<213> ORGANISM: Artificial sequence
<220> FEATURE:
<223> OTHER INFORMATION: Heavy chain (HC) of mAb 0310

<400> SEQUENCE: 27

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 28
<211> LENGTH: 219
<212> TYPE: PRT
<213> ORGANISM: Artificial sequence
<220> FEATURE:
<223> OTHER INFORMATION: Light chain (LC) of mAb 0310

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 29
<211> LENGTH: 451
<212> TYPE: PRT
<213> ORGANISM: Artificial sequence
<220> FEATURE:
<223> OTHER INFORMATION: Heavy chain (HC) of mAb 0336

<400> SEQUENCE: 29

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Ala Val Ile Trp Arg Gly Gly Ser Ile Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Ser His Gly Asn Tyr Val Gly Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

```
Gly Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Leu Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys
    450
```

UNITED STATES PATENT AND TRADEMARK OFFICE
CERTIFICATE OF CORRECTION

PATENT NO. : 11,279,771 B2
APPLICATION NO. : 15/508229
DATED : March 22, 2022
INVENTOR(S) : Petersen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 190 days.

Signed and Sealed this
Fifteenth Day of November, 2022

Katherine Kelly Vidal
*Director of the United States Patent and Trademark Office*